(12) United States Patent
Chen et al.

(10) Patent No.: US 8,066,780 B2
(45) Date of Patent: Nov. 29, 2011

(54) METHODS FOR GASTRIC VOLUME CONTROL

(75) Inventors: Richard Chen, Napa, CA (US); Craig A. Johanson, San Francisco, CA (US); Christopher S. Jones, Menlo Park, CA (US); Reinhold H. Dauskardt, Menlo Park, CA (US)

(73) Assignee: Fulfillium, Inc., Napa, CA (US)

( * ) Notice: Subject to any disclaimer, the term of this patent is extended or adjusted under 35 U.S.C. 154(b) by 1775 days.

(21) Appl. No.: 11/122,315

(22) Filed: May 3, 2005

(65) Prior Publication Data
US 2005/0267595 A1    Dec. 1, 2005

Related U.S. Application Data

(60) Provisional application No. 60/629,800, filed on Nov. 19, 2004, provisional application No. 60/567,873, filed on May 3, 2004.

(51) Int. Cl.
*A61F 2/04* (2006.01)
(52) U.S. Cl. ............... 623/23.65; 623/23.67; 623/23.68; 600/37; 600/116; 606/191; 606/192
(58) Field of Classification Search .............. 606/192, 606/195, 191; 623/23.65, 23.67, 23.68; 600/37, 600/116
See application file for complete search history.

(56) References Cited

U.S. PATENT DOCUMENTS

| | | | |
|---|---|---|---|
| 3,046,988 A | 7/1962 | Moreau et al. | |
| 3,055,371 A | 9/1962 | Kulick | |
| 3,906,959 A | 9/1975 | Cannon | |
| 4,133,315 A | 1/1979 | Berman et al. | |
| 4,246,893 A | 1/1981 | Berson | |
| 4,311,146 A | 1/1982 | Wonder | |
| 4,416,267 A | 11/1983 | Garren et al. | |
| 4,485,805 A | 12/1984 | Foster, Jr. | |
| 4,501,264 A | 2/1985 | Rockey | |
| 4,577,640 A | 3/1986 | Hofmeister | |
| 4,607,618 A | 8/1986 | Angelchik | |
| 4,648,383 A | 3/1987 | Angelchik | |
| 4,694,827 A | 9/1987 | Weiner et al. | |
| 4,723,893 A | 2/1988 | Kiyooka et al. | |
| 4,739,758 A | 4/1988 | Lai et al. | |

(Continued)

FOREIGN PATENT DOCUMENTS
EP    0103481 A1    3/1984
(Continued)

OTHER PUBLICATIONS

International Search Report and Written Opinion of PCT Application No. PCT/US05/41960, dated May 31, 2006, 4 pages total.

(Continued)

*Primary Examiner* — Gary Jackson
*Assistant Examiner* — Michael Mendoza
(74) *Attorney, Agent, or Firm* — Wilson Sonsini Goodrich & Rosati

(57) ABSTRACT

A gastric balloon includes a scaffold structure, one or more internal inflatable compartments within the scaffold structure, and one or more inflatable bladders formed over the space-filling compartment. The gastric balloon may be deployed transesophageally using a gastroscope and is inflated in situ, preferably using a combination of liquid and gas inflation media.

25 Claims, 14 Drawing Sheets

U.S. PATENT DOCUMENTS

| | | | |
|---|---|---|---|
| 4,795,463 | A | 1/1989 | Gerow |
| 4,899,747 | A | 2/1990 | Garren et al. |
| 4,908,011 | A | 3/1990 | Jacobsen et al. |
| 4,983,167 | A | 1/1991 | Sahota |
| 5,084,061 | A | 1/1992 | Gau et al. |
| 5,160,321 | A | 11/1992 | Sahota |
| 5,234,454 | A | 8/1993 | Bangs |
| 5,259,399 | A | 11/1993 | Brown |
| 5,476,005 | A | 12/1995 | Lindegren |
| 5,501,667 | A | 3/1996 | Verduin, Jr. |
| 5,579,765 | A | 12/1996 | Cox et al. |
| 5,833,603 | A | 11/1998 | Kovacs et al. |
| 5,865,801 | A | 2/1999 | Houser |
| 5,993,473 | A | 11/1999 | Chan et al. |
| 6,272,914 | B1 | 8/2001 | Ciotti |
| 6,427,089 | B1 | 7/2002 | Knowlton |
| 6,454,785 | B2 | 9/2002 | De Hoyos Garza |
| 6,579,301 | B1 | 6/2003 | Bales et al. |
| 6,634,216 | B1 | 10/2003 | Yasumoto |
| 6,647,762 | B1 | 11/2003 | Roy |
| 6,656,194 | B1 | 12/2003 | Gannoe et al. |
| 6,733,512 | B2 | 5/2004 | McGhan |
| 6,736,793 | B2 | 5/2004 | Meyer et al. |
| 6,746,460 | B2 | 6/2004 | Gannoe et al. |
| 6,981,980 | B2 * | 1/2006 | Sampson et al. ............. 606/192 |
| 7,033,373 | B2 | 4/2006 | de la Torre et al. |
| 7,033,384 | B2 * | 4/2006 | Gannoe et al. ............. 623/1.11 |
| 7,066,945 | B2 | 6/2006 | Hashiba et al. |
| 2001/0001314 | A1 | 5/2001 | Davison et al. |
| 2001/0010024 | A1 | 7/2001 | Ledergerber |
| 2002/0055757 | A1 | 5/2002 | de la Torre et al. |
| 2003/0171768 | A1 | 9/2003 | McGhan |
| 2004/0044357 | A1 | 3/2004 | Gannoe et al. |
| 2004/0059289 | A1 | 3/2004 | Garza Alvarez |
| 2004/0102712 | A1 | 5/2004 | Belalcazar et al. |
| 2004/0106899 | A1 | 6/2004 | McMichael et al. |
| 2004/0122526 | A1 | 6/2004 | Imran |
| 2004/0186502 | A1 | 9/2004 | Sampson et al. |
| 2004/0186503 | A1 | 9/2004 | DeLegge |
| 2005/0033331 | A1 | 2/2005 | Burnett et al. |
| 2005/0055039 | A1 | 3/2005 | Burnett et al. |
| 2005/0107664 | A1 | 5/2005 | Kalloo et al. |
| 2005/0149186 | A1 | 7/2005 | Roballey et al. |
| 2005/0181977 | A1 | 8/2005 | Hunter et al. |
| 2005/0192614 | A1 | 9/2005 | Binmoeller |
| 2005/0273060 | A1 | 12/2005 | Levy et al. |
| 2006/0004272 | A1 | 1/2006 | Shah et al. |
| 2006/0178691 | A1 | 8/2006 | Binmoeller |

FOREIGN PATENT DOCUMENTS

| | | |
|---|---|---|
| EP | 0246999 A1 | 11/1987 |
| EP | 1177763 A | 2/2002 |
| GB | 2090747 A | 7/1982 |
| GB | 2139902 A | 11/1984 |
| GB | 2384993 A | 8/2003 |
| WO | WO 83/02888 A1 | 9/1983 |
| WO | WO 87/00034 A2 | 1/1987 |
| WO | WO 88/00027 A1 | 1/1988 |
| WO | WO 03/055420 A1 | 7/2003 |
| WO | WO 03/095015 A1 | 11/2003 |
| WO | WO 2005/107641 A2 | 11/2005 |

OTHER PUBLICATIONS

Supplementary European Search Report of EP Application No. 05749678, mailed on Oct. 2, 2009, 3 pages total.

* cited by examiner

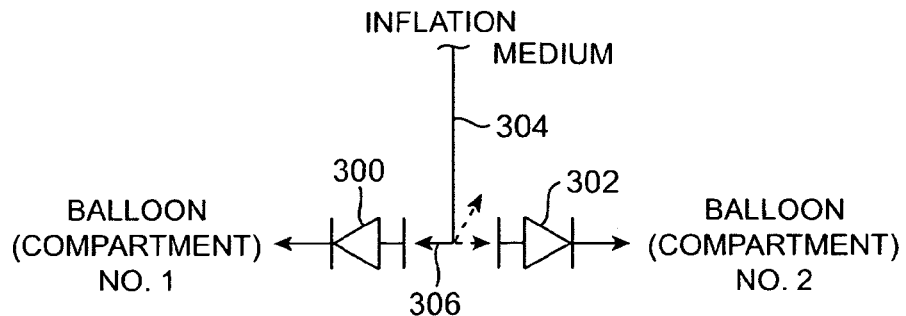
FIG. 16
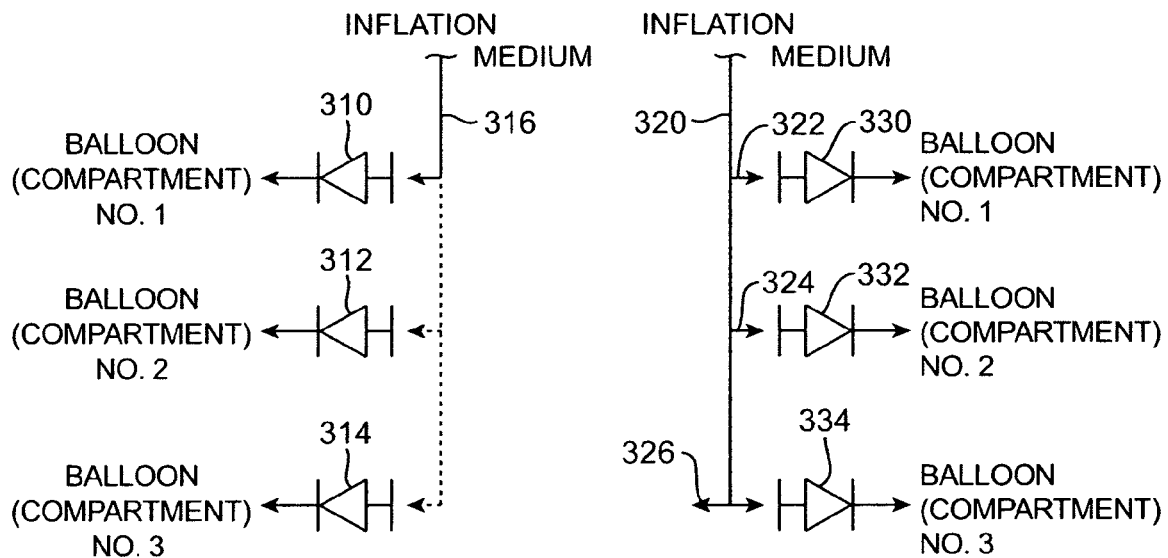
FIG. 17
FIG. 18
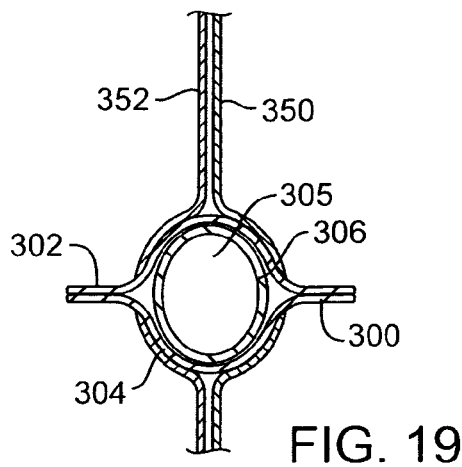
FIG. 19

METHODS FOR GASTRIC VOLUME CONTROL

CROSS-REFERENCES TO RELATED APPLICATIONS

The present application claims the benefit under 35 USC §119(e) of prior provisional application No. 60/629,800, filed on Nov. 19, 2004; and of prior provisional application No. 60/567,873, filed on May 3, 2004, the full disclosures of which are incorporated herein by reference.

BACKGROUND OF THE INVENTION

1. Field of the Invention

The present invention relates generally to medical apparatus and methods. More particularly, the present invention relates to the construction and use of gastric balloons for treating obesity.

Obesity is a serious medical condition and has become a widespread problem in the United States and many other industrialized countries. While many obese patients may be treated by modifications to diet and exercise, a number of morbidly obese patients are resistant to treatment and are candidates for surgical intervention. One surgical approach for treating morbid obesity is referred to as gastric or jejunoileal bypass where a major portion of the gastro-intestinal tract is surgically bypassed. While effective in some patients, gastric bypass procedures can have significant undesirable side affects. Moreover, the initial surgical procedure presents risks associated with open surgery. There are restrictive surgical procedures but they are less effective and still invasive. Consequently, an effective, non-invasive medical treatment with lower risks and minimal side effects is needed for many morbidly obese patients, who cannot tolerate surgical intervention, and most premorbidly obese patients, who have no effective treatment because their condition is not sufficiently severe to qualify them as surgical candidates.

As an alternative to such surgical procedures, the introduction of space-occupying structures into the stomach, often referred to as "gastric balloons," has been proposed. Such gastric balloons may be introduced through the esophagus and inflated in situ in order to occupy a significant volume within the stomach.

Although found to be effective in some cases, the use of gastric balloons has been compromised by a number of deficiencies. The most serious is a sudden or slow deflation of the gastric balloon that can allow the balloon to pass the pyloric valve and enter the intestines. Such unintentional passage of the deflated balloon into the intestines can cause intestinal obstruction and be life-threatening. Consequently, gastric balloons currently marketed outside the US are generally indicated for use of only up to six months.

The risk of deflation is exacerbated by the fact that the patient may not immediately be aware that the balloon has deflated, delaying the patient from seeing a physician. Thus, it would be desirable to provide approaches to allow a patient to detect leakage or impending leakage. Currently to detect leakage, some practitioners add methylene blue dye to the filling fluid, usually saline, prior to inflation. If the methylene blue leaks into the stomach, a blue color will be present in the patient's excrement. This procedure has a number of deficiencies as evidenced by the continued reports of significant rates of intestinal obstruction and excretion of deflated balloons in clinical practice. Slow and intermittent leaks can release such small amounts of dye that the dye is not detectable in the excrement. Faults on the medical professionals' part include mixing concentrations that makes detection unreliable or simply forgetting to mix in the substance prior to inflating the balloon. On the patients' side, many have difficulties detecting slight changes in the color of the excrement, forget to check diligently, or simply find the task psychologically too unpleasant to perform.

Other problems include infections resulting from bacterial colonization of the gastric balloon and lack of adequate sizing of the balloon prior to deployment in a patient's stomach. Additionally, most gastric balloons have been filled with saline or other liquid, making them heavy and uncomfortable within a patient's stomach. The weight of the balloons can cause them to induce gastric hypertrophy and create gastric erosions, ulcers, lesions and abrasions within the stomach at the points where they naturally rest.

For these reasons, it would be desirable to provide improved gastric balloon structures and methods for their use in treating obese patients. The balloons should be durable and the methods and apparatus will preferably be comfortable to the patient and in particular should avoid settling as a heavy weight in the patient's stomach. The gastric balloons and methods for their use should further prevent passage of an accidentally deflated balloon across the pyloric valve and into the intestines, even when the balloon structure is compromised and the balloon looses inflation medium. It would be further desirable if a deflation or impending deflation of the balloon were detectable to the patient in a rapid and reliable fashion. Such a detection system should alert the patient of failure and allow the patient to seek medical help before the balloon has deflated to a size that could pass the pylorus. The compromised device could be then removed or replaced on a timely basis. Additionally, it would be beneficial if the balloons were resistant to bacterial and other microbial growth, thus lessening the risk of infection upon long-term deployment. Other improvements would include balloons and methods for their deployment which allow for proper sizing the balloon and/or trimming or adjusting the balloon size even after deployment. At least some of these objectives will be met by the inventions described below.

2. Description of the Background Art

Gastric balloons and methods for their use in treating obesity are described in U.S. Pat. Nos. 6,746,460; 6,736,793; 6,733,512; 6,656,194; 6,579,301; 6,454,785; 5,993,473; 5,259,399; 5,234,454; 5,084,061; 4,908,011; 4,899,747; 4,739,758; 4,723,893; 4,694,827; 4,648,383; 4,607,618; 4,501,264; 4,485,805; 4,416,267; 4,246,893; 4,133,315; 3,055,371; and 3,046,988 and in the following publications: U.S. 2004/0186503; U.S. 2004/0186502; U.S. 2004/0106899; U.S. 2004/0059289; U.S. 2003/0171768; U.S. 2002/0055757; WO 03/095015; WO88/00027; WO87/00034; WO83/02888; EP 0103481; EP0246999; GB2090747; and GB2139902.

BRIEF SUMMARY OF THE INVENTION

The present invention provides improved gastric balloons and methods for their deployment and use. The balloons will typically have an overall volume or displacement selected to leave a residual volume in the proximal area of the stomach in the range from 10 ml to 100 ml, usually from 20 ml to 40 ml. As discussed in detail below in some embodiments, the volume will be adjustable to optimize treatment on individual patients. The gastric balloons will typically be designed to conform to the natural shape of the gastric cavity while maintaining the normal function of the stomach. The balloon will preferably have a crescent or "kidney" shape to align the balloon wall against the greater and lesser curvatures of the stomach, an oval cross section to conform to the shape of the cavity in the sagittal plane, and delineate a space proximally for the collection of ingested food and another space distally for active digestion.

The gastric balloons include at least two principal structural components. The first principal structural component is an expandable scaffold which helps define a shape conforming to a gastric cavity, typically a crescent or "kidney" shape, when expanded. The scaffold may be self-expanding, e.g. formed from a shape memory metal or shape memory polymer, or may be inflatable with an incompressible fluid, such as saline, water, oil, gel, or other liquid, gel, slurry, solution, or the like. Use of an incompressible inflation or filling fluid helps rigidify the scaffold so that it maintains its shape for extended periods when implanted in the stomach. The expanded shape and side of the scaffold by itself or together with an intact portion of the device form an object that is too large in all orientations, even when compressed in peristalsis, to permit the device to pass the pylorus.

The second principal structural component comprises one or more inflatable or otherwise expandable space-occupying structures or compartments which are secured to the interior and/or exterior of the expandable scaffold. The space-filling structures or compartments assume a space-filling configuration when inflated or otherwise filled or expanded, typically being inflated or filled at least partly with a compressible fluid, typically a gas such as air. Such filling or inflation of the scaffold and/or the space-filling compartment(s) will usually be accomplished from an external pressurized fluid source, but certain gaseous inflation media can be generated in situ within the component by chemical reactions induced by mixing reactants or otherwise initiating a gas-producing chemical reaction. In some cases, the scaffold may form all or a portion of the space-filling structure or compartment.

The scaffold and the inflatable compartment(s) may be joined together in a number of different ways. Self-expanding scaffolds may be disposed inside of, within, or over the walls of the inflatable compartment(s). The scaffolds may have a number of different geometries, including spines, hoops, serpentine elements, plates, shells, or the like. In one particular embodiment, a self-expanding scaffold comprises a single spine which runs axially along one side of the inflatable compartment(s) with a number of generally oval rib structures extending circumferentially around the inflatable compartment(s). In another specific example, the self-expanding scaffold may be in the form of a plurality of interleaved panels which form an umbrella-like cap on one end of the scaffold, typically the end disposed adjacent to the esophagus after deployment. In still another example, the expandable scaffold may be an inflatable saddle or shell which is attached over an outer surface of one or more inflatable compartment(s). In still other embodiments, the scaffold structure may be formed internally with two or more inflatable compartments disposed on the outside of the structure. For example, in a particular embodiment, the scaffold is inflatable and forms an X-shaped cross section with four inflatable compartments, one in each quadrant of the X. Numerous other particular configurations may be made within the principles of the present invention.

The gastric balloons of the present invention may comprise two or more walls or layers or lamina of materials to improve the durability of the device by optimizing the performance characteristics of different materials. This is desirable because the maximal thickness of the entire device in its deflated state such that it can be passed uneventfully through the esophagus is limited and is useful even for a simple, single compartment balloon. Typically, the outermost layer is made of materials, such as silicone rubber, selected primarily for their biocompatibility in the stomach and resistance to an acidic environment and the innermost layer is made of materials selected primarily for their resistance to structural fatigue and permeability to the filling fluid. In addition, use of multiple layers allows the layers to be formed from different materials having different properties, to enhance the performance characteristics of the entire balloon structure. The inner layers could have biocompatibility of a shorter duration than the outermost layer. It may be desirable to enhance the durability further by embedding other structural elements in the layers, such as a mesh made of metal, polymer, or high strength fibers, such as Kevlar®. In the simplest embodiment, the two layers are either bonded together to function as a single wall or left unbonded such that the layers could slide by each other except at certain attachment points.

Optionally, a variety of structural elements may reside in between the outermost and innermost layers. For support, the mesh of high strength fibers, polymer, or metal could constitute another layer in of itself instead of being embedded in the layers. Alternatively, the mesh forms or is a component of the expandable scaffold. One or more layers of materials selected for the optimal balance of biocompatibility, impermeability, rigidity, durability among other criteria could be added to enhance the structural performance characteristics of the device further.

Optionally, a failure detection system may reside in between any of the layers. This is desirable and useful even for a single compartment balloon. An example of a chemical system is based on a thin film or coating of a substance, such as a dye, that is released into the stomach in the event the integrity of the layer external to the substance is compromised and detected upon excretion or regurgitation by the patient. Optionally, different substances may be placed in between different layers so that the particular layer which failed may be identified based on what is detected. Optionally, the substance could be embedded in the layer so that partial breach of the layer would result in the substance be in contact with the stomach contents. Incorporating the substance(s) in the device eliminates a step for the medical professional to measure and mix the substance(s) into the inflation media. Many errors including mixing ineffective concentrations such that detection becomes unreliable, contaminating the different components such that identification of the particular failed component becomes unreliable, confusing the substance(s) with its respective component, or simply forgetting to mix in the substance(s) are prevented. Furthermore, the detection mechanism is standardized for the device and easier for medical professionals other than the person deploying the device to diagnose any failure.

The inflatable compartment(s) may be inflated with compressible fluids (gases), incompressible fluids (liquids), or in some cases mixtures of gases and liquids. When multiple inflatable compartments are used, each compartment may be inflated with the same or different gas(es), liquid(s), and/or mixtures thereof. The use of gas and liquid for gastric balloon inflation has a number of advantages. A principal benefit is the ability to control buoyancy and weight distribution within the balloon, e.g., by filling most of the compartments with a gas and distributing the non-gas inflation medium in other compartments throughout the balloon, the risk of concentrated pressure points against the stomach is reduced. Second, by properly controlling the ratio of air or other gas to saline or other liquid, the gastric balloon can be provided with a desired buoyancy and mass within the stomach. Typically, the ratio of air:liquid can be in the range from 2:1 to 10:1, more preferably within the range from 3:1 to 6:1. Such ratios can provide effective densities relative to water at a specific gravity in the range from 0.09 to 0.5, usually from 0.17 to 0.33, depending on the total volume occupied by the device. Typically, the weight of the filled balloon is in the range from 50 gm to 500 gm, usually being from 50 gm to 450 gm. The use of gastric balloons which are light and less dense will reduce the risk that the balloons will cause abrasion, pressure induced lesions, shearing lesions, or other trauma when implanted in the stomach for extended periods of time.

Optionally, the gastric balloons of the present invention may further comprise at least one separately inflatable or otherwise expandable external bladder formed over an exterior surface of the balloon. The external bladder(s) will be separately inflatable from both the scaffold and the space-filling compartment(s) although they may be attached to or share common walls with either or both of these other principal structural components. The bladder will be positioned on the exterior of the balloon so that it can control either or both of the shape and buoyancy of the balloon as a whole. Typically, the bladder will be inflated at least partly with a compressible gas, typically air or other biocompatible gas. Often, the balloon will be underfilled, i.e., filled with a volume that does not distend or increase the wall tension beyond that of the unfilled bladder.

The expandable scaffold, the inflatable space-filling compartment(s) or structures, and optionally the inflatable bladder(s) may be joined together in the overall gastric balloon structure in a variety of ways. Typically, each component may be separately formed and joined by adhesives, bonding, or by other non-penetrating fasteners, or by other means. Alternatively, all or a portion of these principal structural components may be formed by co-extrusion to provide the desired inflatable volumes. Generally, however, it will be desirable to avoid penetrating fasteners and/or stitching of the principal structural components since such penetrations can compromise the integrity of the components and subject the balloon to leakage over time.

The expandable scaffold upon self-compression or inflation may define one or more internal regions or volumes which receive the inflatable compartment(s). In a first exemplary illustrated embodiment, the scaffold when inflated has a X-shaped cross-section which defines four axially aligned quadrants or channels which would allow relatively free passage of food past the scaffold and through the stomach in the absence of the inflated internal component(s). The inflatable scaffold will usually be formed from a non-distensible material so that it can be fully and generally rigidly inflated by the liquid or other incompressible fluid. The internal components, in contrast, may be formed from an elastic and/or inelastic material to permit its volume to be differentially inflated and adjusted. Usually, the space-filling compartment (s) will leave at least a portion of the channels available for the passage of food, albeit in a restricted or modulated fashion. Alternatively, the shape and structure of the entire device could allow ingested food to pass between the exterior and the stomach wall.

Alternatively, the scaffold could comprise a metal or polymeric scaffold or other open structure which supports the other balloon components but which is not itself inflatable. For example, an open lattice formed from a shape memory material, such as a nickel-titanium alloy, can be compressed and constrained together with the inflatable components for delivering to the stomach. The structure can be self-expanding, i.e. deployed by being released from constraint after delivery to the stomach so that the lattice opens to its memory shape. Such self-expanding scaffolds are preferably collapsible under restraint to a relatively low-profile configuration, typically having a width no greater than about 30 mm, preferably no greater than about 20 mm, in order to permit delivery through a gastroscope or other tubular introducer positioned through the esophagus. For example, the lattice could comprise or consist of one or more axial members having hoop, loop, or rib elements attached along their length(s). Alternatively, the lattice could comprise a plurality of interleaved panels which could be folded and/or rolled into a low width configuration. Other examples include collapsible meshes, collapsible coils, malecot structures, and the like. In contrast, the inflatable components will be deflated to permit introduction in a low profile configuration. The inflatable components can have a variety of geometries including X-shaped cores, inflatable saddles, inflatable caps, and the like. The inflatable components can be deployed by inflation as described elsewhere herein. Alternatively, in some instances, the scaffold might be an outer shell or "exo-skeleton," in some cases simply being a non-distensible sheath or cover which permits inflation of two or more inflatable compartments therein. Still further alternatively, the scaffold may be formed of a solid material for the attachment of the other components of the device in a particular configuration such that collectively, the components assume the desired physical shape or perform the desired functions.

The external bladder(s) may also be formed from elastic and/or inelastic materials, such as silicone rubber and polyethylene terephthalate film (Mylar®), respectively, so that they can be inflated at the end of the procedure to properly position the gastric balloon within the stomach and to provide for proper sizing of the balloon within the stomach. In an illustrated embodiment, the gastric balloon includes one space-filling compartment and one external bladder for each of the four channels formed by the inflatable scaffold, but the number of compartments and/or bladders may differ from the number of channels.

Most embodiments of the present invention will include at least two or more inflatable-space-filling compartments and in some cases may also include one or more inflatable external bladders. The inflation of multiple inflatable compartments and external bladders may be accomplished in a variety of ways. Most simply, each inflatable compartment and inflatable external bladder (if any) could be connected to an independent inflation tube which can be disconnected after inflation. The use of multiple independent inflation tubes allows each inflatable compartment and external bladder to be selectively and independently filled, further allowing filling at different pressures, with different inflation fluids, and the like. The use of multiple inflation tubes, however, is not generally preferred since the tubes, collectively, can have rather a large cross section, and such multiple tubes may interfere with device deployment.

The multiple inflatable compartments and external bladders of the present invention may be filled through a single inflation tube in at least two ways. First, by connecting the inflatable compartments and external bladders in series, for example using a series of one-way valves, inflation through a first inflatable compartment (or external bladder) can sequentially fill additional compartments and bladders in the series as the pressure in each compartment raises and in turn begins to fill the next compartment or bladder in series. Such an approach, however, is generally less preferred since it does not permit selective filling of the compartments and therefore does not permit the pressure and/or composition of the inflation fluid to be controlled and differentiated between the multiple compartments.

Thus, a presently preferred structure and method for filling the multiple compartments and external bladders (if any) of the present invention is to use a selective valve system which can be accessed and controlled by a single inflation tube in order to independently and selectively inflate each of the inflatable compartments and external bladders (if any). Such selective valving system may be constructed in any of at least several ways. For example, an inflation tube having a lateral inflation port near its distal end can be disposed between two, three, or more one-way valves opening into respective inflatable compartments and external bladders. By rotating the inflation tube, the inflation port on the tube can be aligned with one of the one-way valves at a time, thus permitting inflation of the respective compartment or bladder to a desired pressure and with a desired inflation fluid, including liquid inflation fluids, gaseous inflation fluids, and mixtures thereof. The rotatable and selectable inflation tube could be removable. Alternatively, at least a portion of the inflation tube could be permanently mounted within the gastric balloon structure, allowing an external portion of the inflation tube to be removably coupled to the internal portion to deliver the inflation fluids.

In addition to rotatably selectable inflation tubes, the inflation tube could be axially positionable to access linearly spaced-apart one-way valve structures, each of which is connected to a different inflatable compartment or external bladder.

As a still further alternative, a single inflation tube could be rotatably mounted and have several inflation ports along its lengths. Each of the inflation ports could be disposed near one, two, or more different one-way valves communicating with different inflatable compartments and/or external bladders.

In all these cases, the one-way valves will permit inflation by introducing an inflation medium at a pressure sufficiently high to open the one-way valve and permit flow into the associated inflatable compartment or external bladder. Upon removing the pressurized inflation source, the one-way valve will close and remain sealed in response to the increased pressure within the inflatable compartment or external bladder.

In all cases, the inflation tube(s) will be removable from the connected component after the component or multiple components have been inflated. Thus, as described in more detail below, the gastric balloon may be delivered to the stomach in a deflated, low profile configuration, typically through a gastroscope or other transesophageal delivery device. Once in place, the expandable scaffold may be deployed and the inflatable components may be inflated, filled, or otherwise expanded in situ to a desired volume and buoyancy typically by delivering the inflation media through the inflation tubes.

Once the desired inflation size is reached, the inflation tubes may be detached from each of the compartments allowing self-sealing so that the inflation medium remains contained for extended periods of time. To ensure the containment of the medium, valves may be placed in series for any one or more of the inflatable component(s) and/or bladder(s). Other expansion protocols are described elsewhere herein. In particular, component, compartment, or portion of the balloon may be inflated in situ by inducing a gas-generating reduction within the balloon. The reactant(s) may be present in the balloon prior to introduction to the patient or may be introduced using the connecting tubes after introduction to the stomach.

Although one illustrated embodiment of the present invention includes four channels in the inflatable scaffold, it will be appreciated that the present invention will cover gastric balloon structures having only a single passage or channel formed within the scaffold with a single space-filling compartment and single external bladder. Embodiments with two channels, space-filling compartments and external bladders as well as three channels, three space-filling compartments, and three external bladders, as well as even higher numbers will also be within the scope of the present invention.

The dimensions of the scaffold, space-filling compartment (s) or structure(s), external bladder(s), and/or isolated inflation chambers within any or all of these components, will be selected such that the collective volume or physical dimensions of the chambers remaining inflated after deflation of any single chamber (or limited number of chambers) is sufficient to prevent passage of the balloon through the pyloric valve. Usually, the volume(s) will be such that at least two inflatable components and/or chambers within said components could deflate without risk of the "diminished" balloon passing through the pyloric valve, preferably at least three could deflate, and often at least four or more chambers could deflate. The precise volume(s) necessary to prevent passage of the partially deflated balloon structure through the pyloric valve and may vary from individual to individual. A preferred remaining residual inflated volume will be at least about 75 ml, preferably at least about 100 ml and still more preferably at least about 200 ml. After partial deflation, the balloon should have a dimension along any axis or its cross axis of at least 2 cm, preferably at least 4 cm, and most preferably at least 5 cm.

Should any of the principal structural components or any portion(s) thereof fail, then the present invention optionally provides for failure detection. This is desirable and useful even for a single compartment balloon. For example, a substance may be disposed within any or all (at least one) of the internal volumes of the inflatable scaffold, the inflatable space-occupying component(s), and/or the external bladder (or any chambers therein), where the substance is detectable upon release and excretion or regurgitation by the patient. For example, the substance may be a dye, a scented composition, a benign symptom-inducing agent such as polyvinyl pyrolidine (PVP), or the like. The substance will usually be disposed within each of the inflatable volumes of the scaffold, space-occupying compartment, and the external bladder so that failure of any single component or chamber thereof will be provided. Optionally, different substances may be placed in different components so that the particular component which failed may be identified based on what is detected. The substance may be detectable directly by sight, smell, or sensation, and/or by reaction with water in the toilet optionally with the addition of a detection reagent.

A particular failure detection system according to the present invention for gastric balloons comprises a chemical and a chemical vapor detector. Optionally, the system includes at least one other chemical or biochemical that reacts with the chemical, its metabolite, or its reaction product. While this invention is described being used in conjunction with a gastric balloon, it does not exclude use in other biomedical devices where signaling a potential failure or malfunction, especially those potentially leading to a catastrophic loss, is desired. The chemical is disposed in a structural component or in an enclosed volume of the device but released into the body upon a breach in the integrity of the device. After release, the chemical, either in its stable form, metabolite, or reaction product is eventually secreted or excreted into the bodily fluids or exhaled gases. The chemical, its metabolite, or reaction product is sufficiently volatile in its secreted or excreted form so that the vapor concentration is significant enough to be detected by a sensor. Optionally, the system could be improved by subjecting the chemical, its metabolite, or reaction product to certain physical perturbation, such as heat or sonic waves, such that the vapor concentration is altered. Alternatively, the system could be improved through a reaction where the chemical, its metabolite, or reaction product is mixed with other chemicals or biochemicals, including solvents, resulting in a product whose vapor concentration has changed enough to be detected by a sensor. Once the sensor is triggered, a signal indicating the compromised state of the device is sent in order to seek medical assistance on a timely basis. The system requires minimal motivation and judgment in diagnosis and enables detecting device failure in a more consistent and reliable fashion at home. The task of checking one's excrement is thereby avoided.

The chemical could be naturally occurring, synthetic, or made by the human body. Preferably, it is biocompatible to the human body at the concentration that would result if the amount disposed in the device is released completely in one event. Upon such an event, for example, a tear or break in a component, the chemical is released into direct contact with the contents of the body cavity, surrounding tissues or their secretions. It is then absorbed and secreted or excreted in the body fluids or exhaled gases in its stable form. Alternatively, the chemical is metabolized by the body and its metabolites are secreted or excreted in the body fluids. Alternatively, the chemical or its metabolites react with the contents of the body cavity, surrounding tissues or their secretions, or any part of the body until the reactant products are secreted or excreted. The change in vapor concentration of the chemical, its metabolites, and/or reactant products is then detected by the sensor.

Alternatively, more than one chemical could be disposed separately or together as a mixture in the device. After release, the chemicals are then absorbed and secreted or excreted in the body fluids or exhaled gases in their stable forms. Alternatively, at least one of the chemicals is metabolized by the body and its metabolites are secreted or excreted in the body fluids or exhaled gases and the others could have a separate functions, such as a stabilizing agent or catalyst. Alternatively, at least one of the chemicals reacts with the contents of the body cavity, surrounding tissues or their secretions or any part of the body until the ultimate reactant products are secreted or excreted. Alternatively, at least one of the chemicals or its metabolites or reactant products react with each other in the presence of the contents of the body cavity, surrounding tissues or their secretions or any part of the body until the ultimate reactant products are secreted or excreted. At least one of the products of the reaction is then secreted or excreted in its stable form or as metabolites in the body fluids or exhaled gases. Used as a mixture, the change in vapor concentration of one or more of the chemicals, their metabolites, or their reaction products could be more readily detected to increase sensitivity of the detection system or the change in vapor concentration of more than one increases the specificity.

Optionally, more than one chemical or more than one mixture of chemicals may be disposed in different parts or components in the device so that more than one part or component which has been compromised may be identified based on which chemical was detected.

Optionally, more than one chemical or more than one mixture of chemicals may be disposed in the same part or component in the device so that the degree of compromise may be determined based on which chemical or a combination of chemicals was detected.

The chemical or mixture of chemicals can be disposed anywhere in the device or its components but typically in the wall of the balloon or any part that is more likely to be compromised. It can be distributed evenly throughout the structure or in an irregular fashion but preferably widely enough to cover the potential sites of failure. The preferred configuration is a fine lattice or continuous film of the chemical or chemical mixture embedded in the wall or in between layers of the wall covering the entire balloon, thereby conforming to the shape of the balloon. Such a configuration optimizes the performance of the system in detecting failures early. As the site of the breach cannot be predicted, a breach is unlikely to be missed by covering the entire balloon. Compromise of the balloon typically starts with a somewhat linear split or tear in surface of the balloon wall from mechanical fatigue. As the split propagates, it will soon expose more and more lines of the lattice or area of the film to the stomach contents. Consequently, as the size and seriousness of the breach increases, the more the chemical is released and the probability of detection increases. Being embedded in the wall of the balloon further enables detection before a full breach of the entire thickness of the balloon wall.

Optionally, the performance could be enhanced by subjecting the chemical, its metabolite, or reactant product to certain physical perturbation, such as heat or sonic waves, such that the vapor concentration is altered. For example, the vapor concentration could be increased in a well heated room or by a toilet flush. Alternatively, the system could be enabled through a reaction where the chemical, its metabolite, or reactant product is mixed with other chemicals or biochemicals (which need not be biocompatible) introduced exogenously and the vapor concentration of the exogenous reaction product is detected by the sensor. For example, a supply of the exogenous chemical can be packaged like a solid toilet bowl cleaner and placed in the water tank. The chemical is dispensed consistently and reliably as a reactant into the bowl. The reaction product in the resulting concentration is at a level necessary for detection but could be bioincompatible had the reaction occurred in the body.

The chemical vapor detector is based on either the natural olfactory sense or the commercially available technology of so-called "electronic nose", with which certain chemicals can be detected at levels from parts per million to parts per billion. The detector is preferably powered by batteries and portable enough to be worn on a wristband or belt or can be placed conveniently near the toilet. Upon sensing the chemical, its metabolite, or the reaction product, the detector will alert the patient to seek medical assistance or alert medical professionals directly through other devices, such as Bluetooth linked to an autodial telephone. The alarm could be auditory, such as beeping sounds, visual, such as flashing LED's or a LCD display, sensory, such as vibrations, or preferably a combination of any or all of the above. Optionally, the detector could have different auditory, visual, sensory, or different combinations to identify the source of the detected breach, especially with more than one chemical is used. For example, LED's of different colors or different sounds could be used. The alarm could further indicate the seriousness of the breach. For example, when multiple probes detect a breach, the volume of the alarm would increase to a higher level.

The present invention further provides a wireless failure detection system for gastric balloons and methods for their deployment and use. While this invention is described being used in conjunction with a gastric balloon, it does not exclude use in other biomedical devices where signaling a potential failure or malfunction, especially those potentially leading to a catastrophic loss, is desired. The failure detection system comprises two probes, a wireless transmitter, and a wireless detector. While this invention is described using radio frequency as the signal transmission of choice, it does not exclude other carrier waves, such as light or acoustic, or via physical properties, such as magnetism or temperature. The probes are connected electronically to the wireless transmitter, which can emit a signal recognized by the detector. Upon direct contact with the stomach contents by the probes, the transmitter is enabled to signal the detector to notify the patient that the integrity of the balloon is compromised and, therefore, seek medical assistance. The system requires minimal motivation and judgment in diagnosis and enables detecting device failure in a more consistent and reliable fashion at home. The task of checking one's excrement is thereby avoided. The system can be designed to function in a variety of algorithms to notify the patient in a simple, unequivocal fashion. For example, in a toggle algorithm, the transmitter is either on in the static state or preferably off in order to reduce the need for power. Upon direct contact with the stomach contents, the probe causes the transmitter to turn the signal off or preferably on to be able to send a wireless signal on a continuous basis. The wireless signal or lack thereof is recognized by the detector to notify the patient that the integrity of the balloon is compromised.

Alternatively, the algorithm could be based on time, amplitude, frequency, or some other parameter. For example, the transmitter may send a wireless signal at a predetermined time interval in its static state. The detector recognizes the length of the interval as normal and the existence of the signal as the system in working order. Upon direct contact with the stomach contents by the probes, the transmitter is enabled to send the same signal at different time intervals or a different signal, which is recognized by the detector to notify the patient that the integrity of the balloon is compromised. The lack of a signal is recognized by the detector to notify the patient of a detection system malfunction and potential compromise of the integrity of the balloon.

Optionally, more than one probe or more than one type of probe may be placed internally in different parts or components in the device so that the particular part or component which failed may be identified based on which probe was activated. The transmitter would send different signals for the receiver to display the source of the failure.

The internal probe could be of any shape and is disposed in the interior or preferably in the wall of the balloon. The preferred configuration is a fine lattice or continuous film of the detection material embedded in the wall or in between layers of the wall covering the entire balloon, thereby conforming to the shape of the balloon. Such a configuration optimizes the performance of the system in detecting failures early. As the site of the breach cannot be predicted, the probe would be unlikely to miss detecting the breach by covering the entire balloon. Compromise of the balloon typically starts with a somewhat linear split or tear in surface of the balloon wall from mechanical fatigue. As the split propagates, it will soon expose more and more lines of the lattice or area of the film to the stomach contents. Consequently, as the size and seriousness of the breach increases, the probability of detection increases. Being embedded in the wall of the balloon further enables detection before a full breach of the entire thickness of the balloon wall. There are further advantages. As the size of the balloon that can pass uneventfully through the esophagus is limited, typically no larger than 2 cm in diameter in its deflated cylindrical shape, the volume of detection material per area of balloon wall is reduced. Furthermore, the lattice or film could provide additional structural support to the device.

The detection material could be any metal, polymer, fiber, or combination thereof, with or without any coating that can generate an electrical charge or enable flow of electric current when in contact with the stomach contents. For example, an electrical charge could be generated from a non-toxic chemical reaction when the lattice exposed underneath a tear comes in contact with the acidic contents. Flow of electric current could be enabled when two ends of an electric circuit are in contact with electrolytes in the stomach. For example, a charged lattice is embedded in the wall and the ground is the external probe on the surface of the balloon or the lattice is ground and the probe is charged. When the lattice is exposed to the electrolytes in the stomach content, the circuit is closed. Alternatively, the lattice and ground could be separate from each other but interlaced in the wall of the device. Preferred materials include non-corrosive, biocompatible metals and elastomers containing electrically conductive particles.

The transmitter can be a simple wireless signal generator triggered by an electric current or preferably a transponder using the well-established RFID technology, i.e., produces a wireless signal when triggered by an interrogating signal. The electric charge generated or the electric current enabled by the probe in contact with the stomach contents enables the transmitter to emit or causes it to emit a wireless signal. Typically, the transponder is powered by the interrogating radio frequency signal so that no power source of its own is required. Alternatively, the transmitter could be powered by a micro battery or by the electrical power generated by a chemical reaction. For protection from degradation by an acidic and electrolyte solution and become potentially toxic, the transmitter or transponder circuit is encased in a highly resistant material, such as silicon rubber or stainless steel. The transmitter or transponder circuit can be placed on the exterior, embedded in the wall, or preferably in the interior of the balloon for further shielding from chemical degradation and mechanical stress. It can be placed in any orientation, preferably in the plane where the antenna is most sensitive and the transmitter is most effective in sending and receiving signals through body tissue.

The wireless signal from the transmitter is recognized by a detector external to the body. The detector could be simply a receiver tuned to the transmitter's signal or, preferably, a combination of both a transmitter of a signal to interrogate the transponder and a receiver to distinguish the different signals from the transponder. The detector is preferably powered by batteries and portable enough to be worn on a wristband or belt or can be placed conveniently near a place where the patient spends most of his time. Upon receiving a signal that a breach has occurred, the detector will alert the patient to seek medical assistance or alert medical professionals directly through other devices, such as Bluetooth linked to an autodial telephone. The alarm could be auditory, such as beeping sounds, visual, such as flashing LED's or a LCD display, sensory, such as vibrations, or preferably a combination of any or all of the above.

Optionally, the detector could have different auditory, visual, sensory, or different combinations to identify the source of the detected breach, especially with more than one probe or more than one type of probe. For example, LED's of different colors or different sounds could be used. The alarm could further indicate the seriousness of the breach. For example, when multiple probes detect a breach, the volume of the alarm would increase to a higher level.

As a further option, at least a portion of the exterior of the inflatable balloon will be coated or impregnated with an antimicrobial and/or adhesion resistant agent. Preferably, the entire exposed surface of all components of the balloon will be so coated or impregnated to inhibit colonization of the balloon by bacteria or other microbes, and/or reduce possible accumulation of food particles on the device. Suitable antimicrobial agents include polyethylenetetrafluoride (PTFE), and antibiotics.

The present invention further provides methods for treating obesity in a patient. The methods comprise introducing a gastric balloon structure to the patient's stomach. An inflatable scaffold which forms part of the balloon is then filled with an incompressible fluid to provide a fixed support geometry. At least a portion of a separate space-filling compartment is then filled at least partly with a compressible fluid, typically a gas such as air, nitrogen, or the like, within the remainder (if any) being filled with an incompressible material, such as a liquid, gel, slurry, or the like. In this way, the buoyancy of the balloon may be controlled within the limits described above.

The methods of the present invention will usually further comprise determining the size of the gastric cavity and selecting a gastric balloon of proper size prior to introducing the balloon to the stomach. Such size determination may comprise visually examining the gastric cavity, typically under direct observation using a gastroscope, but alternatively using fluoroscopy, ultrasound, x-ray or CAT scanning, or any other available imaging method. An estimate of the dimensions of the stomach and the size of the device can be made by direct observation of the interior of the stomach immediately prior to deployment. Alternatively, the dimensions of the feeding stomach, which is generally larger than the resting stomach, and the size of the device will be determined at an earlier session where the patient has consumed or swallowed a biocompatible filling medium, e.g., water, contrast medium, food, etc. A sufficient amount of filling medium will be consumed so that the imaging technique can detect full relaxation of the stomach during feeding and estimate its dimensions and size.

Introducing may then comprise passing the gastric balloon in a deflated configuration into the stomach through the same gastroscope. Alternatively, the deflated balloon could be introduced into the gastric cavity via an attachment to an orogastric or nasogastric tube. The balloon will be oriented so that the scaffold will open with curved geometry conforming to the curve of the gastric cavity. Typically, the scaffold will be released from constraint to self-expand or will be filled through a removable inflation tube attached to the scaffold, where the inflation tube may be removed after filling. The scaffold will then be sealed or will more typically be self-sealing upon detachment of the filling tube(s) to prevent loss of the inflating liquid medium. Similarly, the space-filling compartment(s) will also typically be filled through one or more inflation tube(s) removably attached to the compartment(s), where the tube(s) are removed after the compartment(s) have been filled with the desired medium, typically a mixture of liquid and gas sources. Further, the external bladder(s) will typically be filled through one or more inflation tube(s) generally as described above for both the scaffold and the space-filling compartment(s).

After all the principal structural components of the gastric balloon have been inflated or otherwise expanded and the associated inflation tubes released, any other anchors or tethers attached to the balloon may also be released, leaving the balloon free to "float" within the patient's stomach. By properly selecting the ratio of liquid inflation medium to gas inflation medium, as discussed above, the weight, distribution, and the buoyancy of the gastric balloon will be such that the balloon rests within the stomach without exerting undue pressure at any particular point, thus reducing the risk of abrasions or other trauma to the stomach lining. The inflated gastric balloon may be left in place for extended periods of time, typically as long as weeks, months, or even years.

After the balloon has been inflated and left in place, it may become desirable to adjust the size and/or buoyancy of the balloon for purposes of patient comfort, efficacy, or other reasons. To perform such adjustments, the balloon will be transesophageally accessed, typically using a gastroscope with suitable working tools introduced therethrough. For example, the balloon may be grasped with graspers and inflation tubes may be suitably attached or docked to inflation ports on the balloon structure. Typically, the inflation ports will all be located near the end of the gastric balloon structure which is oriented toward the top of the stomach so that they are readily accessed through the gastroscope. After attachment with the inflation tube, the inflation medium can be introduced and/or extracted, depending on whether the particular structural component is to be enlarged, deflated, or have a buoyancy adjustment. Optionally, an incising instrument could be introduced through the gastroscope to penetrate and deflate any filled compartment to reduce the overall volume of the device and improve accommodation of the device. Typically, these compartments are small to allow minor adjustments without jeopardizing the integrity of the device itself.

In addition to adjusting the size and/or buoyancy of the gastric balloon, it may become desirable or necessary to remove the balloon completely. To effect such removal, the balloon will again be accessed transesophageally, typically using a gastroscope. The balloon will first be grasped or secured using a grasping tool. Then, one or more surfaces of the balloon may be penetrated or breached in order to release the contents of the balloon into the stomach. The contents will be biocompatible gasses or liquids so that release into the stomach will not be a concern. After the contents of the compartments have been released, the balloon may then be pulled through the patient's esophagus, typically by pulling with the grasping tool. It may be possible to pull the deflated gastric balloon through the working channel of the gastroscope, but more often the balloon will simply be withdrawn through the esophagus as the gastroscope is withdrawn. Optionally, a sheath or other protective cover may be placed over the deflated balloon in order to reduce the risk of trauma or injury to the esophagus upon withdrawal.

BRIEF DESCRIPTION OF THE DRAWINGS

FIGS. 16-18 are flow diagrams illustrating several valving systems suitable for inflating gastric balloons having multiple inflatable compartments and optionally internal bladders in accordance with the principles of the present invention.

FIG. 19 illustrates an exemplary structure for valving according to FIG. 16.

DETAILED DESCRIPTION OF THE INVENTION

Figure 1:
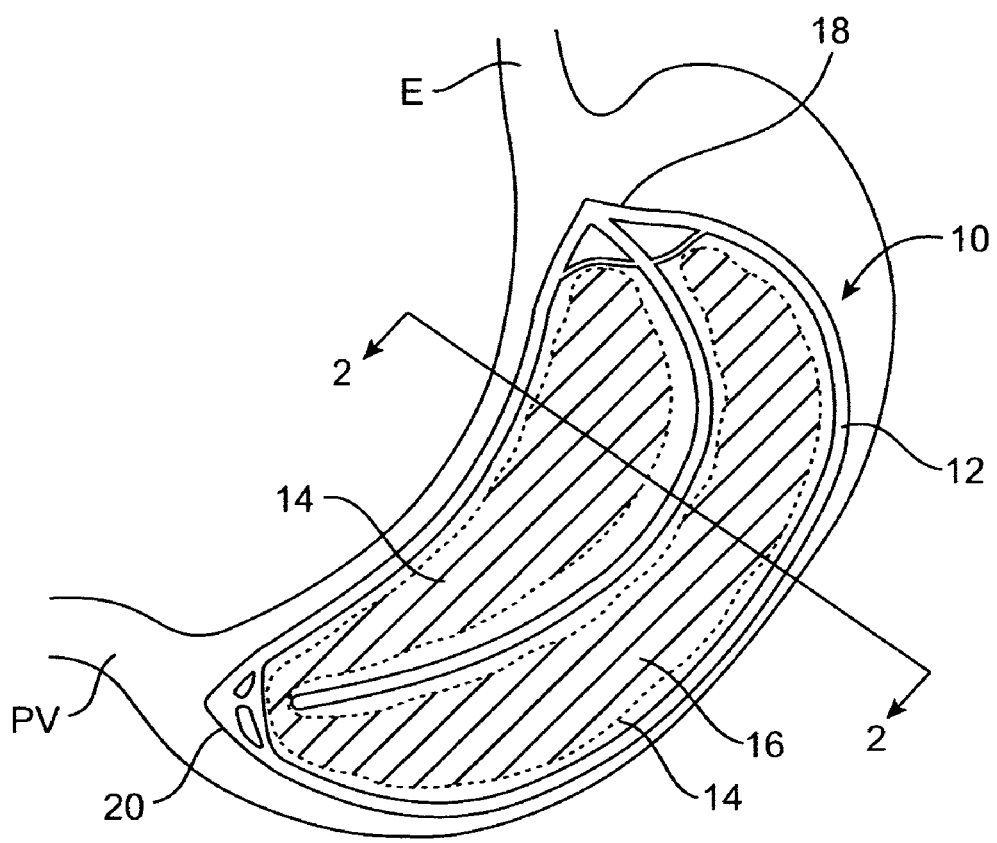
FIG. 1 is a side view of a gastric balloon constructed in accordance with the principles of the present invention, shown deployed in a stomach.
Figure 2:
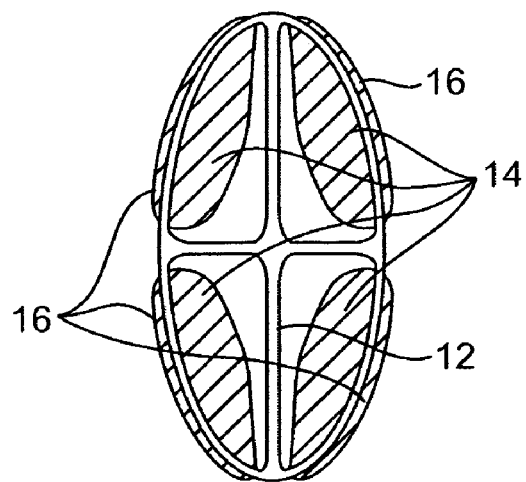
FIG. 2 is a cross-sectional view taken along line 2-2 in FIG. 1.

Referring now to FIGS. 1 and 2, a gastric balloon 10 constructed in accordance with the principles of the present invention comprises an inflatable scaffold structure 12, four inflatable space-filling compartments 14, and four inflatable external bladders 16. Referring in particular to FIG. 2, the inflatable scaffold 12 has a X-shaped cross-section and defines four generally axially oriented channels or quadrants, each of which receives one of the four inflatable space-filling compartments 14. The four inflatable external bladders 16 are mounted over the inflatable space-filling compartments 14, and the balloon 10 includes an upper cage 18 and lower cage structure 20 which permit grasping of the balloon using grasping tools, as will be described in more detail below. In its deployed configuration, the gastric balloon 10 has a crescent or curved shape which conforms to the interior shape of a gastric cavity, with the upper cage structure 18 oriented toward the esophagus E, the lower cage structure 20 oriented toward the pyloric valve PV.

Figure 3:
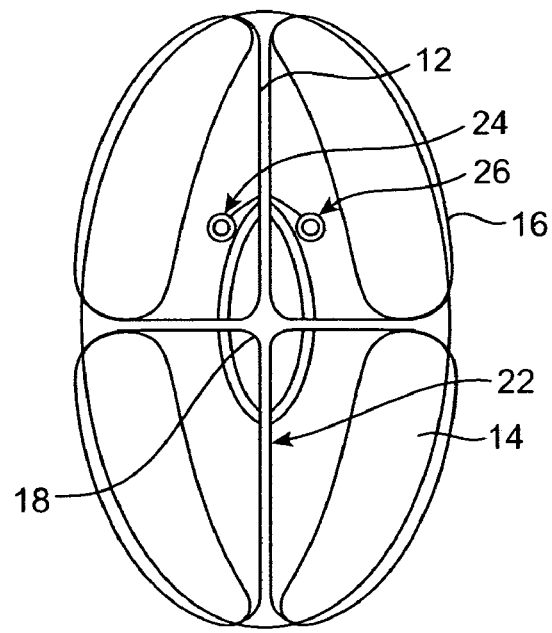
FIG. 3 is a top view of the gastric balloon of FIG. 1, illustrating the inflation ports or nipples.

Referring now to FIG. 3, the inflatable scaffold structure 12 is provided with at least one inflation port or nipple 22 while the inflatable space-filling compartments 14 are provided with a separate port 24 and the inflatable external bladders are provided with a separate inflation port 26. Although not illustrated, the scaffold, internal components, and external bladders could have isolated, inflatable volumes therein, each of which would be attached to a separate inflation tube. By "subdividing" the volume of the various principal structural components, the risk of accidental deflation of the balloon is further reduced.

Figure 4A:
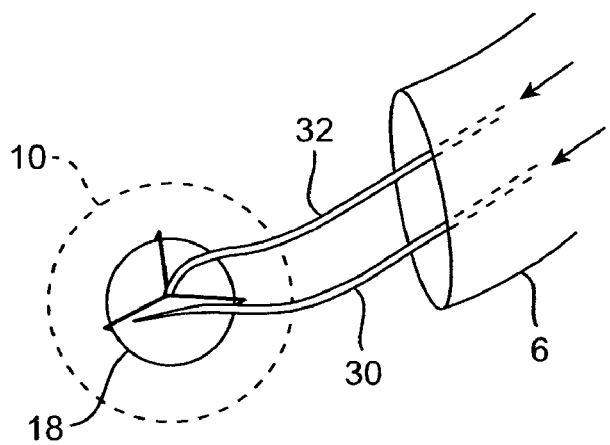
FIGS. 4A and 4B illustrate use of tools introduced through a gastroscope for inflating and deflating the gastric balloon of FIG. 1, respectively.

As illustrated in 4A, after the gastric balloon 10 is introduced in its deflated configuration into the gastric cavity, the inflatable structural components could be inflated using a single inflation tube 30 introduced through the gastroscope G, or orogastrically or nasogastrically by itself or using an orogastric or nasogastric tube. Typically, the upper cage 18 will be held by a grasper 32 which can selectively hold and release the gastric balloon 12 during inflation and subsequent deployment. Shown in FIG. 4A, inflation tube 30 can be selectively coupled to any one of the inflation ports 22, 24, or 26, and the desired inflation medium introduced therethrough. Inflation tube 30 will be suitable for delivering either liquid or gas inflation media, typically including saline, water, contrast medium, gels, slurries, air, nitrogen, and the like.

Usually, the inflatable scaffold structure 12 will be inflated entirely with a liquid or other incompressible medium, such as a gel, slurry, or the like. In contrast, the inflatable space-filling compartments 14 will at least partly be inflated with air or other gas. Often, however, the inflatable space-filling compartments will inflated with a mixture of gas and liquid in order to control the buoyancy of the balloon 12. Finally, the external bladders 16 will typically be inflated with gas in order to provide a relatively soft outer surface which can reduce trauma and abrasion.

The various structural compartments of the balloon may be made from the same or different materials. Usually, the inflatable scaffold structure 12 will be formed from a non-distensible (non-stretching) material so that it may be inflated to become a relatively rigid structure. Alternatively, or additionally, the structures may be formed from stiffer materials and/or be reinforced to increase the rigidity when inflated.

In contrast, the inflatable space-filling compartments 14 and the inflatable bladders 16 may be formed in whole or in part from softer elastomeric materials in order to allow inflation flexibility, both in terms of size and density of the combined inflation media. The elastic nature of the external bladders allows the peripheral dimensions of the gastric balloon to be adjusted over a significant range by merely controlling inflation volume. Elastic inflatable space-filling compartments can allow the amount of space occupied in the interior of the balloon to be adjusted, for example to adjust the amount of volume filled by the balloons within the quadrants defined by the scaffold structure 12. Alternatively, the volume of incompressible fluid introduced into non-elastic structures may be sufficient to control the volume being occupied.

As an alternative to using a single inflation tube, each of the inflation ports 22, 24, and 26 could be pre-attached to separate inflation tubes. In such cases, after inflation of each structural component is completed, the necessary inflation tube could then be withdrawn through the gastroscope G, leaving the gastric balloon 10 in place.

Figure 4B:
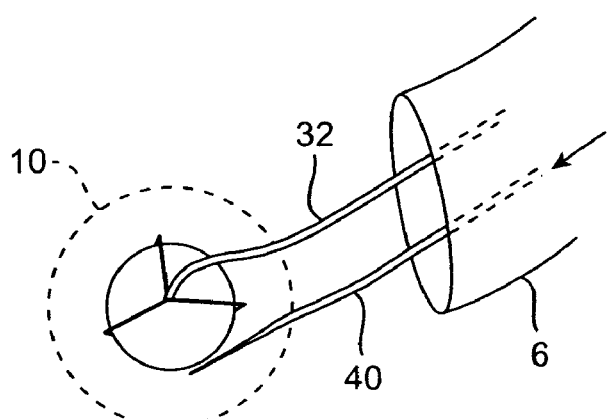

Referring now to FIG. 4B, the balloon 10 can be deflated while grasping the tip 18 of the balloon with grasper 32 through gastroscope G using a blade structure 40 introduced through the gastroscope. The blade structure 40 will preferably be used to make one or more penetrations or breaches within each of the inflatable components of the gastric balloon, including the inflatable scaffold, the inflatable space-filling compartment(s), and the inflatable external bladder(s)

Referring now to FIGS. 5A-5E, gastric balloon 10 is introduced to a patient's stomach S using a gastroscope G introduced through the esophagus E in a conventional manner. Standard procedures for preparing and introducing the gastroscope are employed, including checking for ulcerations in the esophagus and performing further examination if warranted.

Figure 5A:
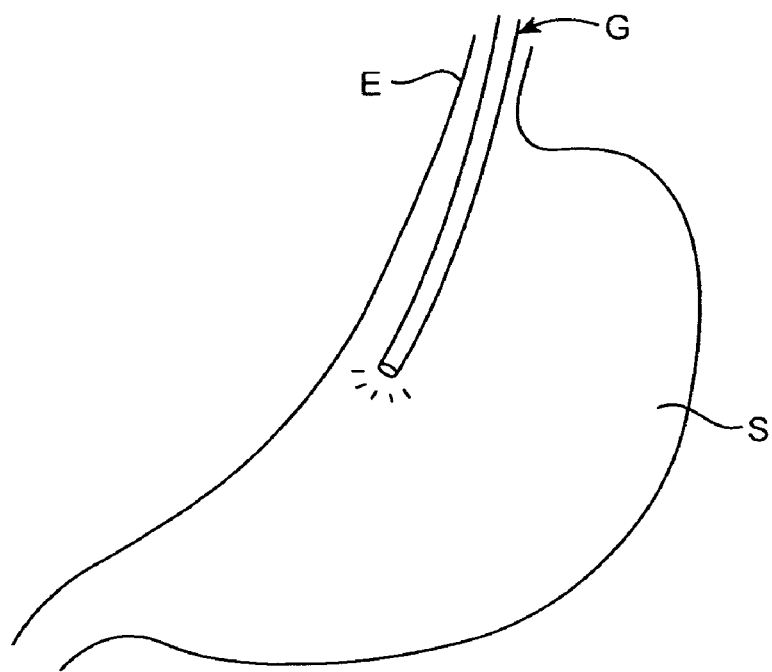
FIGS. 5A through 5E illustrate a complete deployment protocol according to the methods of the present invention.
Figure 5B:
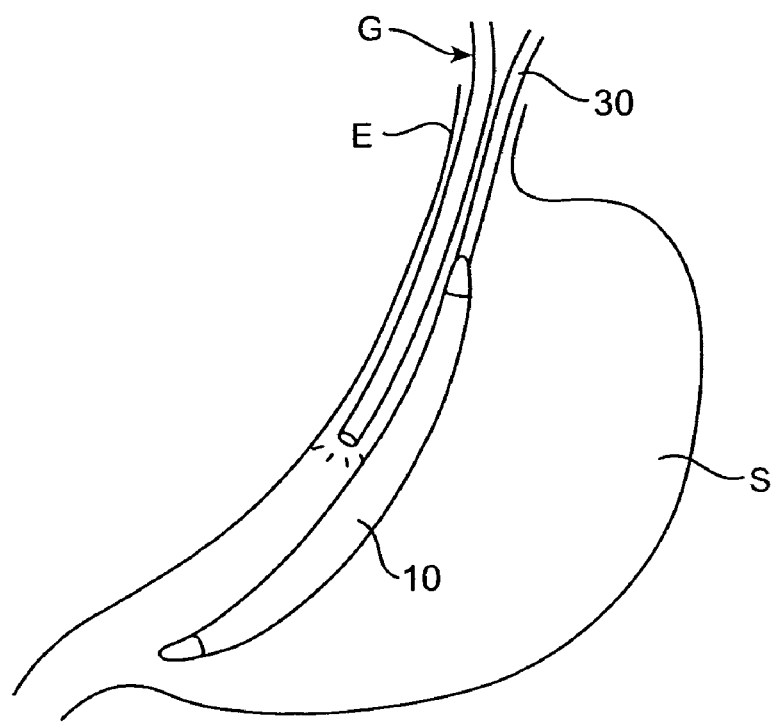
Figure 5C:
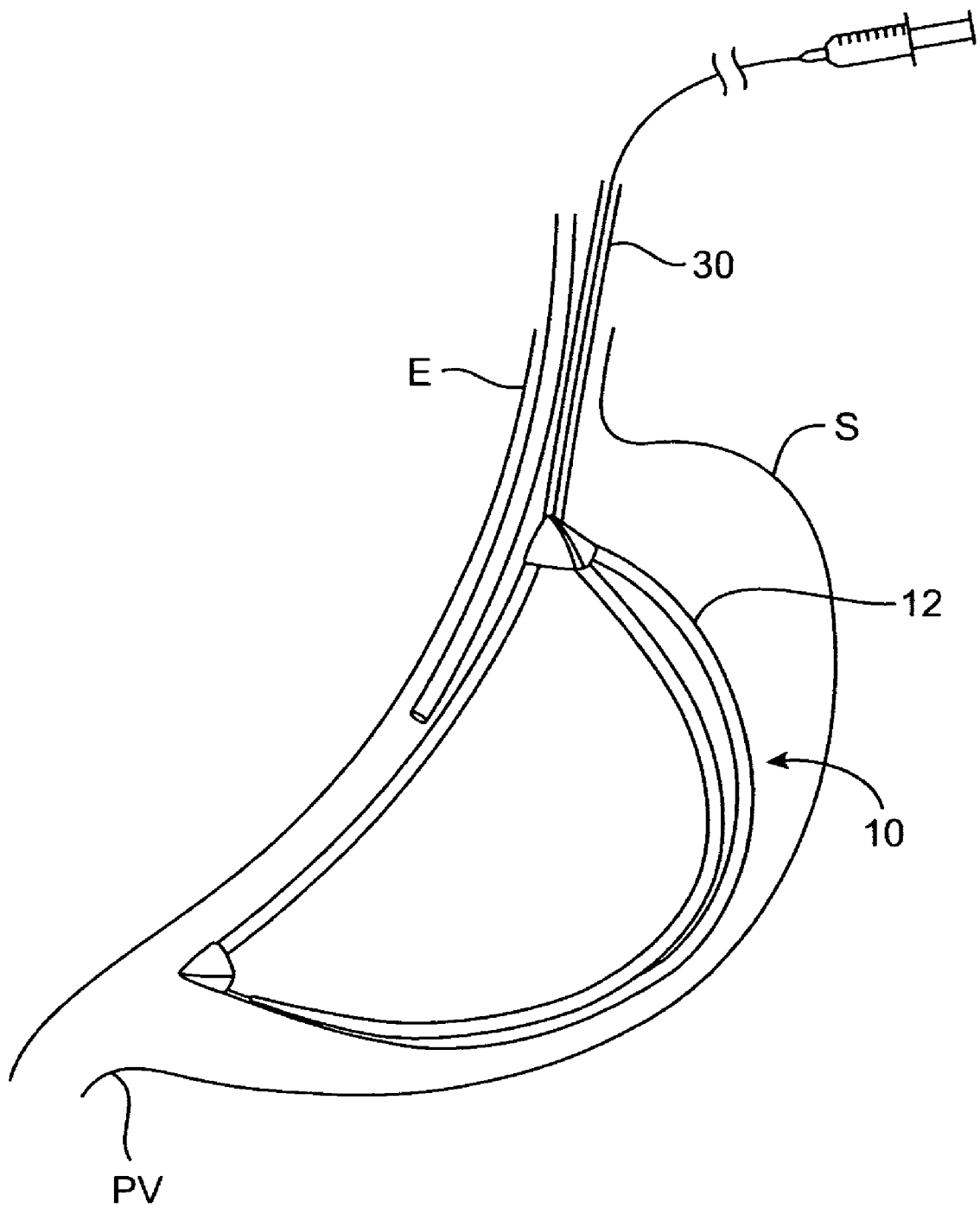
Figure 5D:
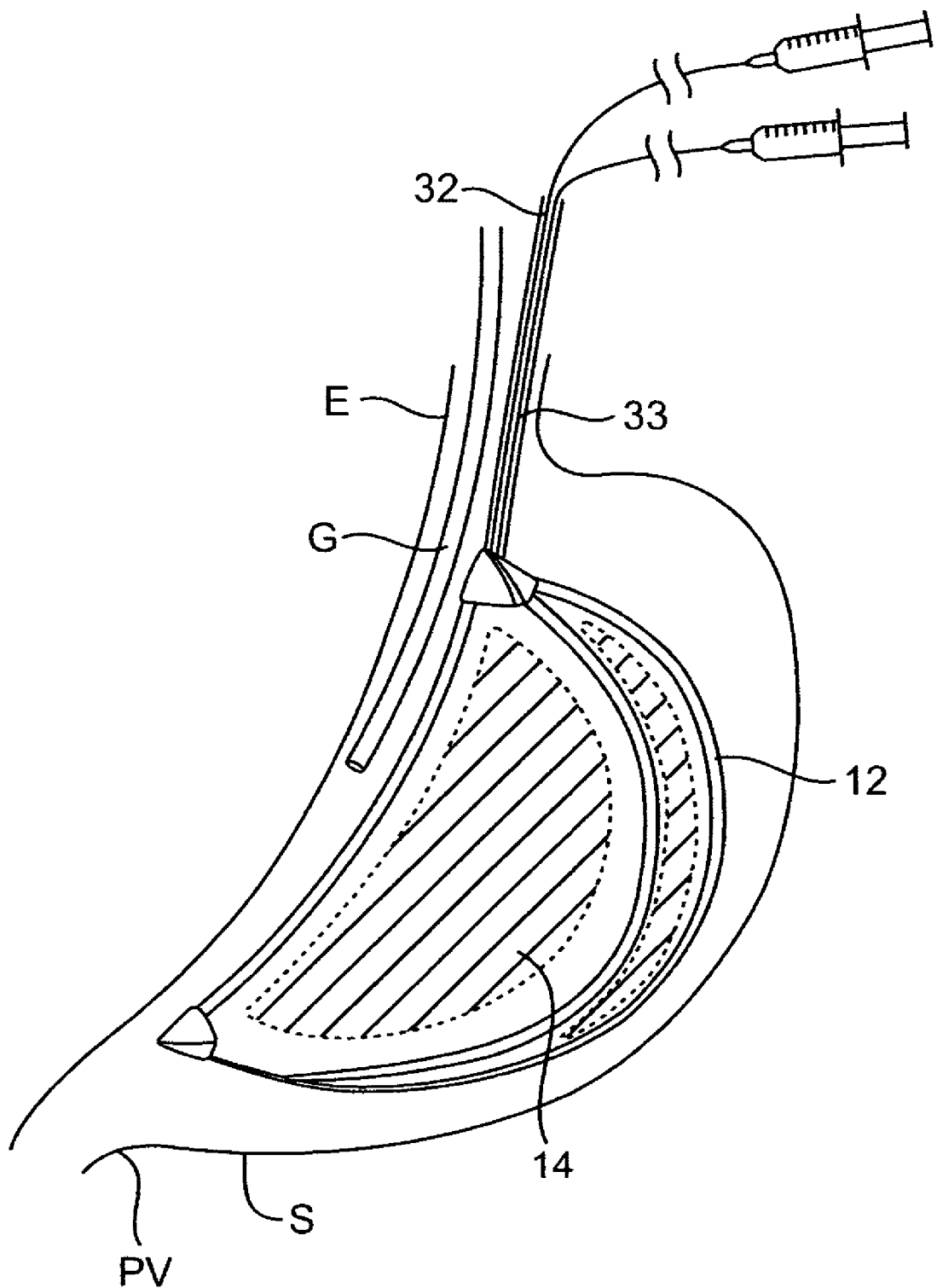

After introducing the gastroscope G, the size of the gastric cavity within stomach S can be estimated and a balloon of an appropriate size selected. The balloon 10 is then also introduced through the esophagus E (orogastrically or nasogastrically) using an appropriate catheter or optionally using the inflation tube(s) which will be used to inflate the balloon. After the entire balloon is confirmed to be in the stomach at a proper orientation, typically using the gastroscope G, the various components of the balloon 10 may be inflated as shown in FIGS. 5C and 5D. First, the inflation tube 32 attached to the port which is coupled to the scaffold 12 is inflated, typically using saline or other incompressible liquid until the scaffold structure becomes relatively rigid, as shown in FIG. 5C. During this inflation, the balloon 10 is held by at least an inflation tube 32 and may optionally be held by additional inflation tube(s) and/or a grasper 32.

After the scaffold 12 has been inflated, an additional syringe is used to inflate the space-filling compartments through a second inflation tube 33, as shown in FIG. 5D. The space-filling compartments, again, will typically be inflated with a combination of saline or other liquid and air or other gas in order to achieve the desired density of the inflation medium therein. The external bladders 16 will be inflated in a similar manner, typically using air or other gas inflation medium only.

Figure 5E:
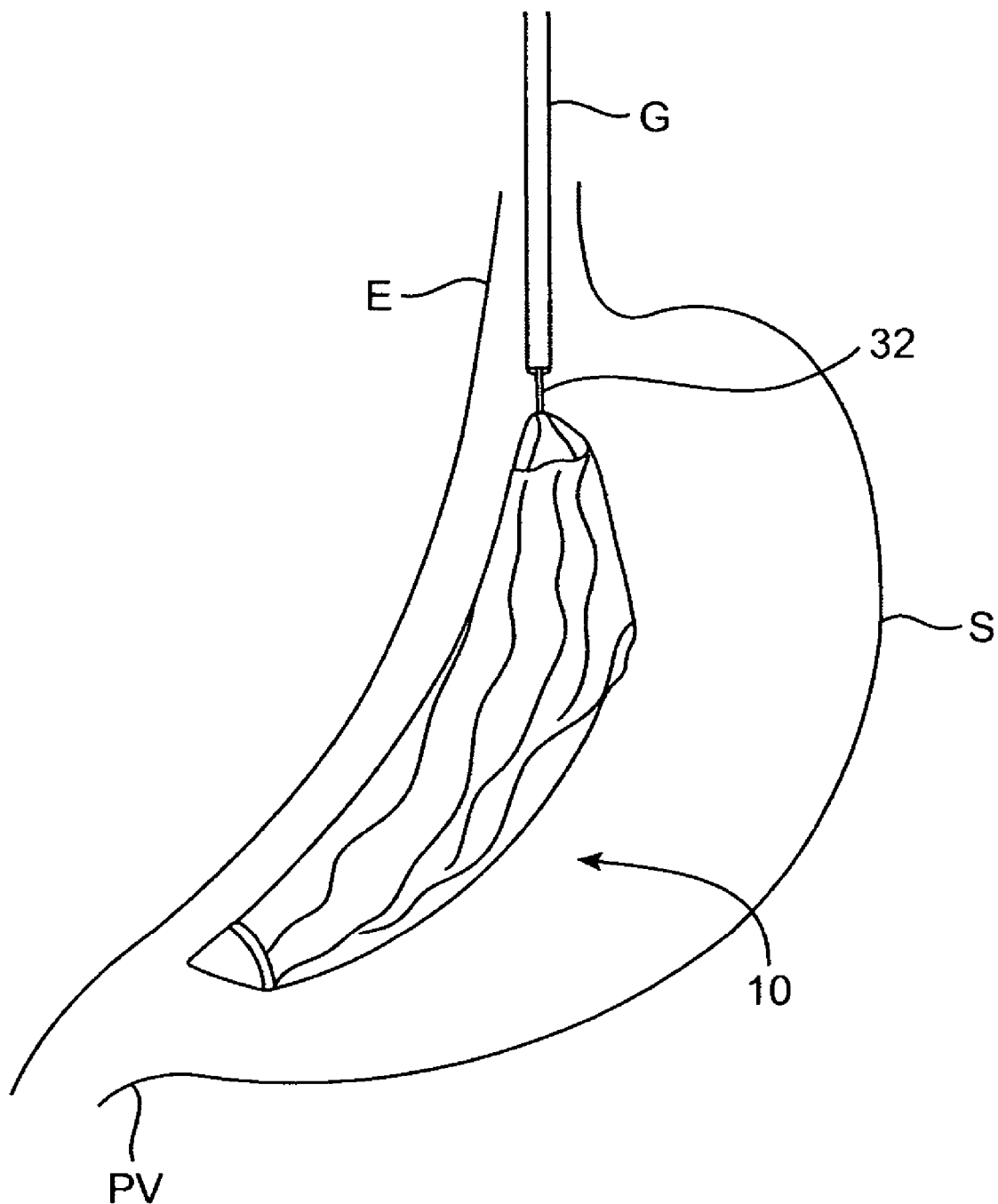

When it is desired to remove the gastric balloon 10, the balloon may be deflated as previously discussed and removed through the esophagus using a grasper 32 passing through the gastroscope G, as shown in FIG. 5E. Typically, the balloon will be pulled out using both the gastroscope and the grasper 32.

Figure 6:
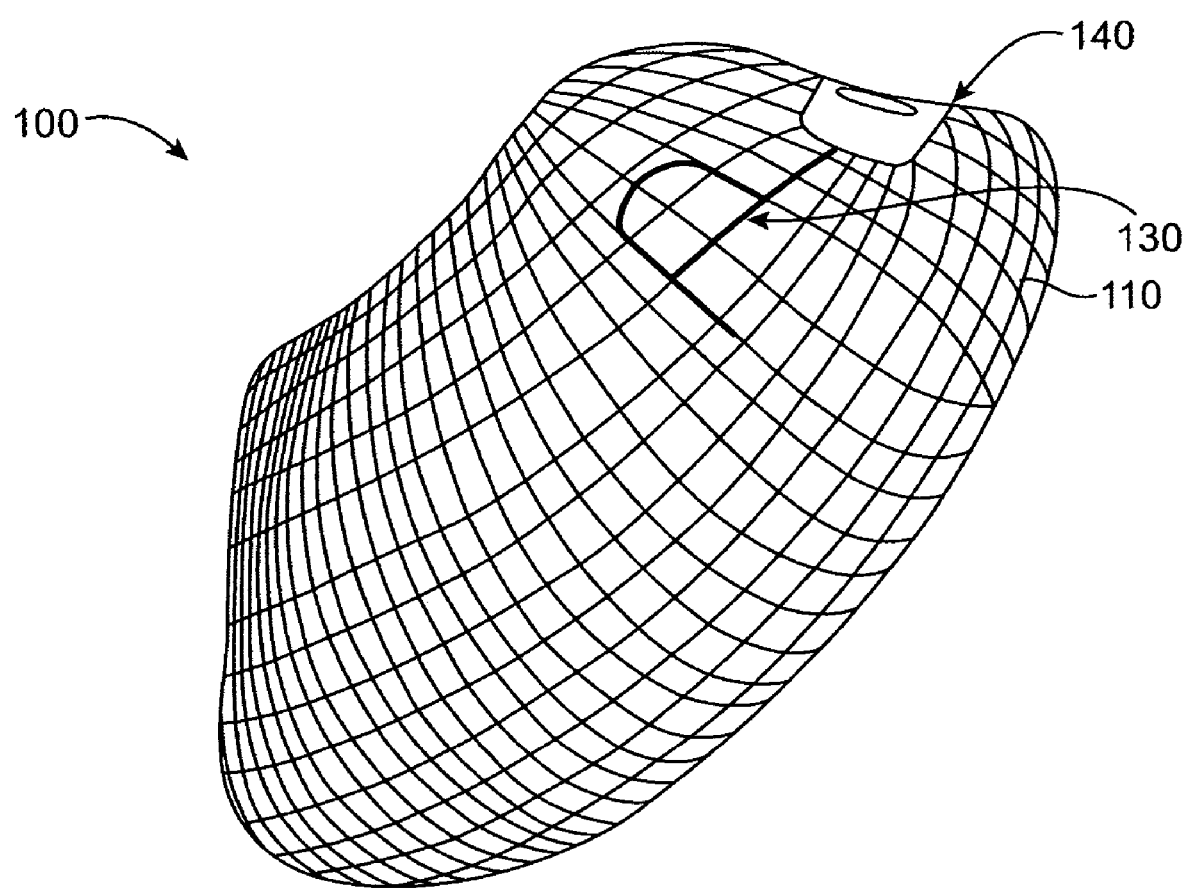
FIG. 6 is a frontal view of a gastric balloon with an optional material incorporated in a lattice configuration in the wall of the device constructed in accordance with the principles of the present invention.
Figure 7A:
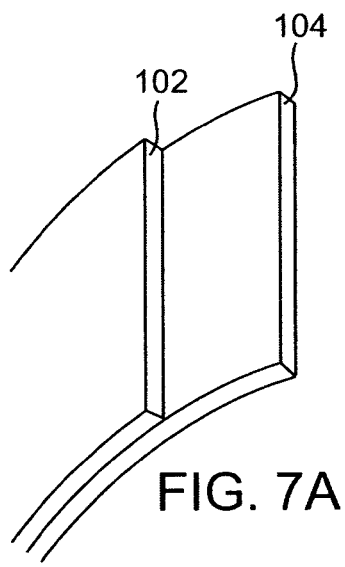
FIGS. 7A through 7C are enlarged, peeled-back, cross-sectional views of a portion of the multi-layered wall of the gastric balloon of FIG. 6 constructed in different configurations in accordance with the principles of the present invention.

Referring now to FIG. 6, a gastric balloon 100 of a single compartment constructed in accordance with the principles of the present invention. As illustrated in FIG. 7A, the wall of the balloon comprises at the minimum an outermost layer 102 and innermost layer 104. The layers are manufactured by either dipping a mold successively into solutions of different materials that dry and cure or preferably by successive precision injections of materials into a mold. Typically, the outermost layer 102 is made of one or more materials, such as silicone rubber, selected primarily for their non-abrasiveness, biocompatibility in the stomach, and resistance to an acidic environment. Typically, the innermost layer 104 is made of materials selected primarily for their resistance to structural fatigue and impermeability to the filling fluid. The inner layer 104 could have biocompatibility of a shorter duration than the outermost layer. The two layers are either bonded together to function as a single wall or left unbonded such that the layers could slide by each other except at certain attachment points.

Figure 7B:
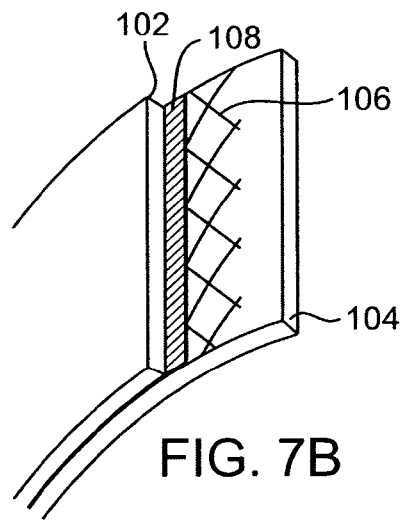

Referring now to FIG. 7B, it may be desirable to enhance the durability further by incorporating other structural elements in the layers, such as a mesh 106 made of metal, polymer, or high strength fibers, such as Kevlar, or the scaffold (not shown). The mesh could constitute a separate layer as illustrated in FIG. 7B or instead, could be embedded in one of the layers of material, as shown embedded in layer 104 in FIG. 7C. A mesh 106 could inhibit the propagation of a tear in the layers. Many of these materials are radio-opaque which enables imaging clearly the entire shape of the device using plain diagnostic X-ray radiography.

Figure 7C:
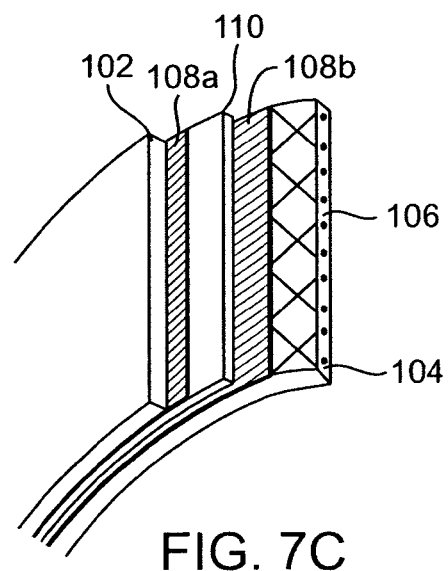

As illustrated in FIGS. 7B and 7C, in addition to layers of 102 and 106, one or more layers, 108 and 110, of materials selected for the optimal balance of biocompatibility, impermeability, rigidity, shear resistance among other criteria could be added to enhance the structural performance characteristics of the device further.

Referring now to FIG. 7B, layers, 108 and 110, could also represent other materials incorporated to enable or enhance certain functional performance characteristics of the device. Instead of disposing the detection marker in the enclosed volume of the balloon, the marker may reside in between any of the layers either in a thin film or in a lattice configuration. It is also possible to dispose the marker in the open spaces in the mesh (not shown). A thin film or coating of a substance that is detectable upon excretion or regurgitation by the patient, such as a dye, would be released into the stomach in the event the integrity of the layer external to the substance is compromised. For example, the substance that forms thin film is released into the stomach when a breach, such as a tear, occurs in layer 102.

Referring now to FIG. 7C, as an optional configuration, different substances, 108a and 108b, may be placed in between different layers so that the particular layer which failed may be identified based on what is detected. For example, if 108a were detected in the excrement, one would deduce that layer 102 has been breached but layer 110 has not. This would constitute a situation where medical assistance can be provided on an elective basis. Once 108b is detected in the excrement, one would deduce that at the minimum, layers 108 and 110 have both been compromised leaving only layer 104 as possibly the last line of defense. This would represent a medical emergency where the device should be removed before complete failure.

Another failure detection system comprises a chemical substance and a chemical vapor detector, an "electronic nose," that detects a change in vapor concentration of the substance, its metabolite, or any of its reaction products. Optionally, it includes at least one other chemical or biochemical that reacts with the chemical, its metabolite, or any of its reaction products to enhance the sensitivity and/or specificity of detection. When used in conjunction with a biomedical device, the system represents a method to detect early potential failure or malfunction involving a structural breach. While this invention is described being used in conjunction with a gastric balloon, it does not exclude use in other biomedical devices where signaling a potential failure or malfunction, especially those potentially leading to a catastrophic loss, is desired.

Referring again to FIG. 6, the gastric balloon 100 includes a chemical substance in a lattice configuration 110 incorporated in the wall of the balloon. The chemical substance could be naturally occurring, synthetic, or made by the human body. As magnified in FIG. 8, the chemical substance can be disposed in a fine lattice configuration 110 and/or in a thin film configuration 112 in the wall of the balloon in between two or more layers, e.g., outermost layer 102 and innermost layer 104. The chemical substance can be also disposed in any enclosed space in the device (not shown)

Figure 8:
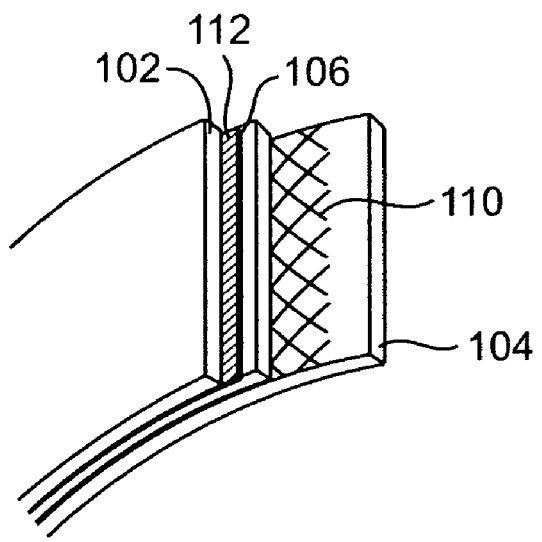
FIG. 8 is a magnified cross-sectional view with an element in a thin film configuration and in a lattice configuration in between layers of materials used in construction of the balloon.

After the balloon 100 is deployed in the stomach, the chemical substance comes in contact with and is released into the surrounding tissue and body fluids upon a breach in the integrity of the wall. As illustrated in FIG. 8, the chemical substance 112 comes in contact with and is released when there is a tear in the outermost layer 102 of the balloon wall. After release, the chemical substance, either in its stable form, its metabolite, or reaction product is eventually secreted or excreted into the bodily fluids. The chemical substance, its metabolite, or reaction product is sufficiently volatile in its secreted or excreted form so that the change in vapor concentration of the secreted or excreted form is significant enough to be detected by a chemical vapor sensor. The chemical vapor detector is based on either the natural olfactory sense or the commercially available technology of so-called "electronic nose", with which certain chemicals can be detected at levels from parts per million to parts per billion.

Figure 9:
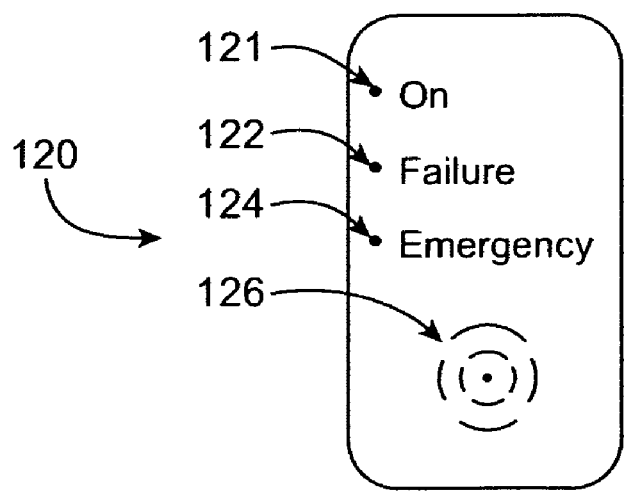
FIG. 9 is a frontal view of the portable detector with an example of a failure display and auditory alarm constructed in accordance with the principles of the present invention.

Referring now to FIG. 9, the sensor, power source, and electronic circuit is enclosed within detector 120. The detector 120 is preferably powered by batteries and portable enough to be worn on a wristband or belt or can be placed conveniently near the toilet. Upon sensing the chemical substance, its metabolite, or a reaction product, the detector will alert the patient to seek medical assistance. The alarm could be visual, such as lit or blinking LED's 122 and 124, and can designate different levels of urgency depending on what was detected. For example, a lit LED 122 could indicate that chemical substance 112 in FIG. 8 has been detected. It can be deduced that layer 102, external to 112 has been breached. Since there are still more than two layers to breach before complete breach of the balloon wall, medical assistance can be provided on an elective basis. In the same fashion, a lit LED 124, could indicate chemical substance 110 has been detected, and therefore layer 106 external to 110 has been breached. Since only layer 104 remains as the last barrier to complete breach of the wall and when that occurs cannot be predicted, the device needs to be removed on an emergent basis. A power light 121 is provided to assure the device is on.

Shown in FIG. 9, the alarm 126 could also be auditory, such as beeping sounds, or sensory, such as vibrations, or preferably a combination of any or all of the above. Optionally, the detector could have different auditory, visual, sensory, or different combinations to identify the source of the detected breach, especially with more than one chemical substance used. The alarm could further indicate the seriousness of the breach. For example, when breaches are detected, the volume of the alarm would increase to a higher level.

Optionally, the system could be improved by subjecting the chemical, its metabolite, or reaction product to certain physical perturbation, such as heat or sonic waves or a toilet flush, such that the vapor concentration is altered. Alternatively, the system could be improved through a reaction where the chemical substance, its metabolite, or reaction product is mixed with other chemicals or biochemicals, including solvents, resulting in a product whose vapor concentration has changed enough to be readily detected by a sensor.

Optionally, detecting the change in vapor concentration of more than one of the chemical substance, its metabolites, or its reaction products could increase the sensitivity and/or specificity of the detection system.

Another failure detection system comprises two electrical probes, wireless transmitter, and a wireless detector. While this invention is described using radio frequency as the signal transmission of choice, it does not exclude other carrier waves, such as light or sonic, or via physical properties, such as magnetism or temperature. When used in conjunction with a biomedical device, the system represents a method to detect early potential failure or malfunction involving a structural breach. When used in conjunction with a biomedical device, the system represents a method to detect early potential failure or malfunction involving a structural breach. While this invention is described being used in conjunction with a gastric balloon, it does not exclude use in other biomedical devices where signaling a potential failure or malfunction, especially those potentially leading to a catastrophic loss, is desired.

Referring now to FIG. 6, the gastric balloon 100 includes two electric probes. Probe 130 is on the external surface in contact with the surrounding tissues, body fluids, and contents of the stomach. The lattice configuration 110 provides the second probe incorporated in the wall of the balloon. The probe material could be any metal, polymer, fiber, or combination thereof, with or without any coating that can generate an electrical charge or enable flow of electric current when in contact with the stomach contents. The probes are connected electronically to the wireless transmitter 140, but are separated from each other by at least one layer of non-conductive material in the balloon wall. The transmitter can be a simple wireless signal generator triggered by an electric current or preferably is a transponder using the well-established RFID technology, i.e., produces a wireless signal in response when triggered by an interrogating signal. In the intact state, 130, 110, and 140 represent an open electrical circuit and the transmitter is enabled to transmit a base signal.

As magnified in FIG. 8, the internal probe can be in a fine lattice configuration 110 or in a thin film configuration 112 in the wall of the balloon in between, at the minimum two layers, an outermost layer 102 and innermost layer 104. The internal probe can be also disposed in any enclosed space in the device (not shown). In the configuration described in FIG. 8, probes 130 and 110 and transponder 140 represent one open circuit and probes 130 and 112 and transponder 140 represent a second open circuit. Each open circuit enables the transponder to transmit a base signal.

After the balloon is deployed in the stomach, the external probe 130 is in contact with the surrounding tissue and body fluids and stomach contents. Upon a breach in the integrity of the wall, such as a tear in the outermost layer 102 as illustrated in FIG. 8, the leakage of physiologic fluid or stomach contents with electrolytes into the tear forms a salt bridge that closes the circuit formed probes 130 and 112 and transponder 140. Once the circuit is closed, a toggle is switched in the transponder, which will be enabled to transmit a "layer 102 breach" signal. Tears through layer 106 in the balloon wall will allow leakage of physiologic fluid or stomach contents with electrolytes into the tear forming a salt bridge that closes the circuit formed probes 130 and 110 and transmitter 140. Closing this circuit switches another toggle in the transponder, which will be enabled to transmit a "layer 106 breach" signal.

Figure 10:
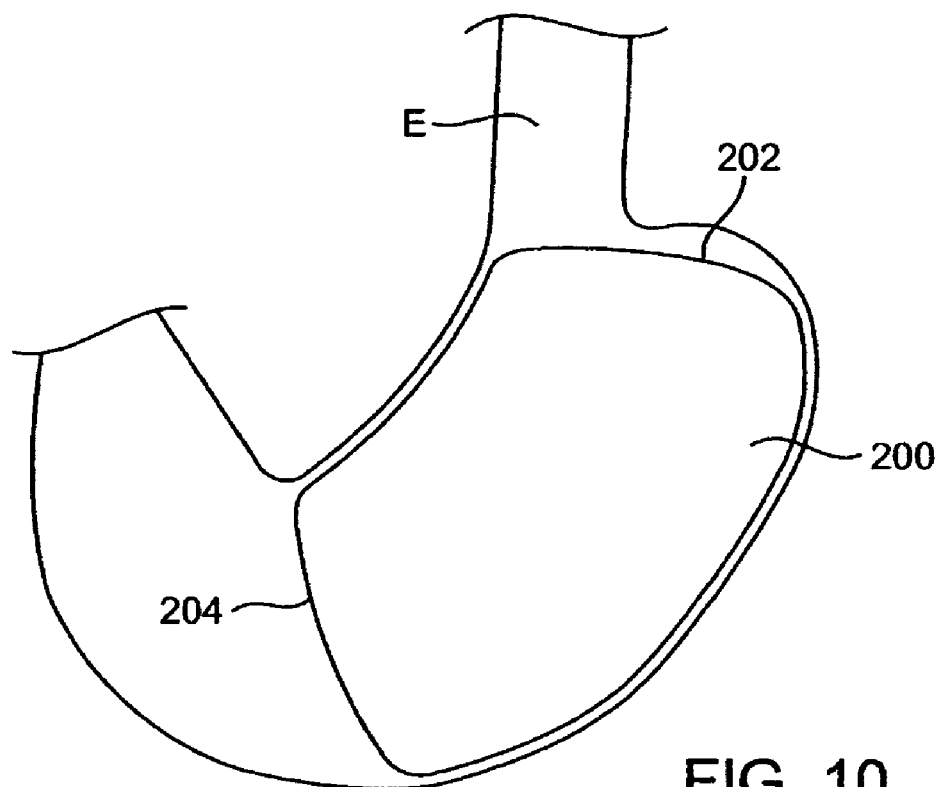
FIG. 10 illustrates an alternative balloon geometry in accordance with the principles of the present invention, shown deployed in a stomach.

FIG. 10 illustrates an alternative crescent-shaped balloon geometry suitable for use in the gastric balloons of the present invention. Gastric balloon 200 has a generally flat or truncated upper surface 202 which is positioned adjacent to the esophagus E. A lower end 204 is also generally flat or truncated. These flat ends 202 and 204 are distinguishable from the more tapered ends of the prior gastric balloon embodiments. Although illustrated schematically as a single unit or structure, it will be appreciated that the balloon 200 will usually comprise multiple independently inflatable space-filling compartments and optionally further comprise external inflatable bladders. The geometry shown in FIG. 10 is intended to illustrate the peripheral shape of the device including all components.

Figure 11:
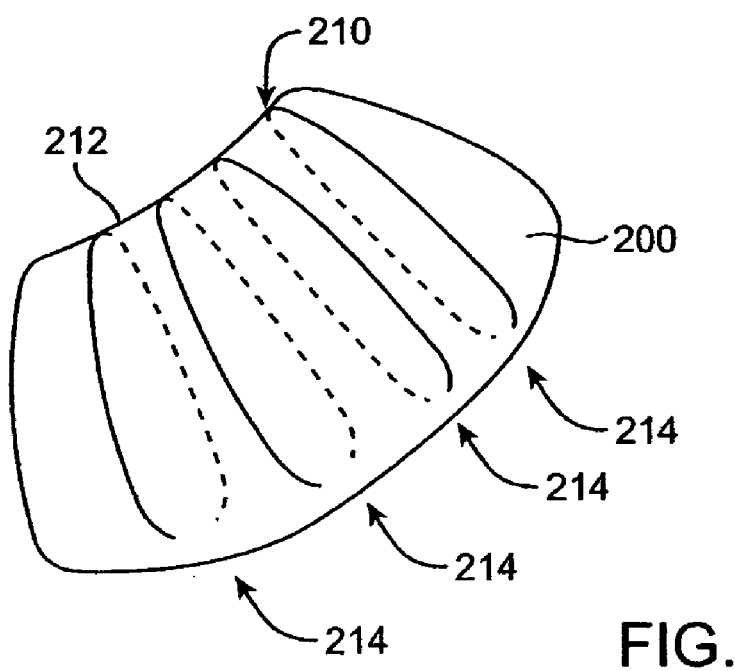
FIG. 11 illustrates first embodiment of a self-expanding scaffold for the balloon geometry of FIG. 10.
Figure 12:
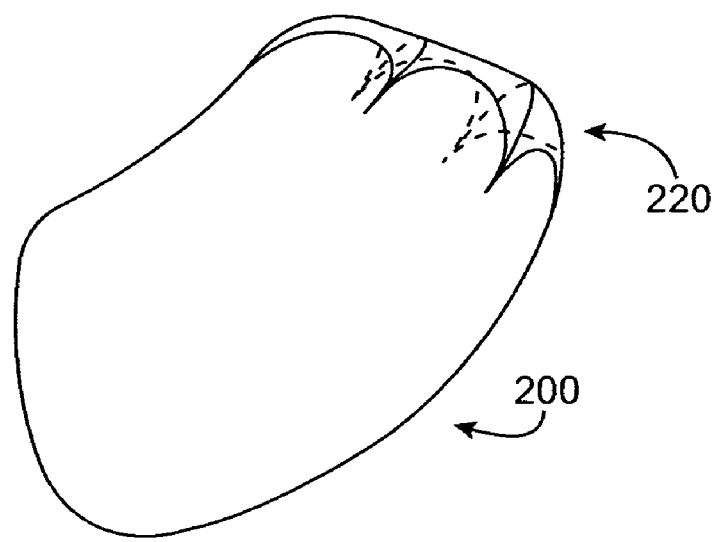
FIG. 12 illustrates a second embodiment of a self-expanding scaffold geometry for a balloon having the geometry of FIG. 10.

Referring now to FIGS. 11-15, gastric balloon structures having the geometry of balloon 200 in FIG. 10 may be deployed using a number of different expandable scaffolds. For example, as shown in FIG. 11, the balloon structure 200 may include an external "exo-skeleton" 210 comprising a spine 212 and a plurality of ribs 214 extending laterally from the spine. The spine 212 and ribs 214 are preferably made from elastic components, such as nickel titanium alloys or other super elastic materials, permitting them to be folded and compressed to a small width for introduction. The scaffold will then be deployed by releasing the scaffold from constraint after it has been positioned within the stomach.

The balloon 200 may also be mated with an end cap 220. The end cap 220 may include, for example, a plurality of interlaced panels which can be folded down to a low profile configuration for delivery. The panels may be composed of elastic polymers, shape memory metals, shape memory polymers, or the like. The use of end caps 220 is particularly useful when the balloon will itself comprise a single compartment. The end cap will prevent accidental passage of the balloon through the pylorus even upon rapid deflation of the balloon.

Figure 13:
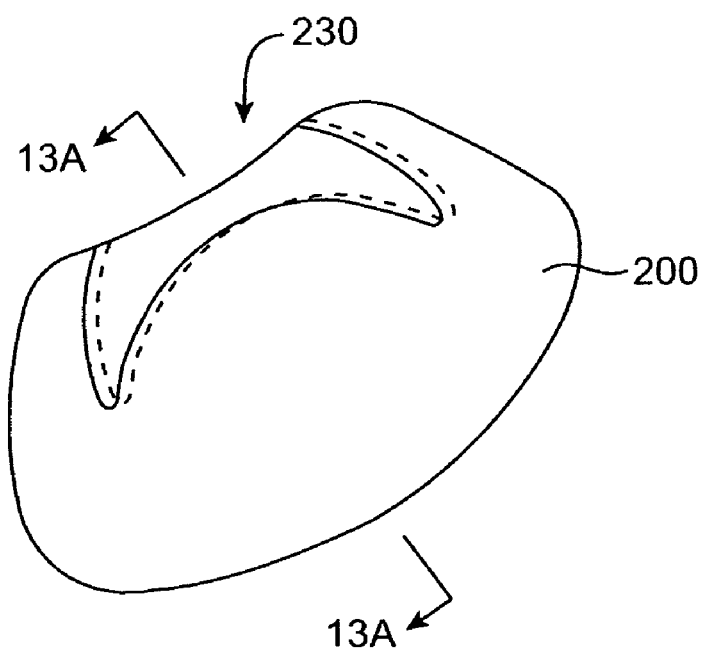
FIG. 13 illustrates an inflatable scaffold suitable for use with a balloon having the geometry of FIG. 10.
Figure 13A:
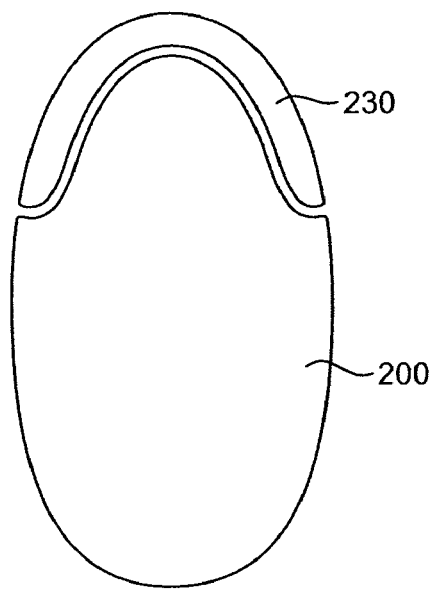
FIG. 13A is a cross-sectional view taken along line 13A-13A of FIG. 13.

The balloon 200 may also be mated to an inflatable scaffold 230, which may be conveniently formed into the shape of a saddle, as shown in FIGS. 13 and 13A. The balloon 200 may comprise one, two, or more separate inflatable compartments. Each of these compartments, as well as the inflatable scaffold 230, will require separate inflation, preferably using one of the valving mechanisms described hereinbelow. The inflatable scaffold 230 could have other configurations as well, such as being in the form of a lattice with a central inflatable spine and multiple arms disposed laterally outwardly about the remainder of the balloon 200.

Figure 14:
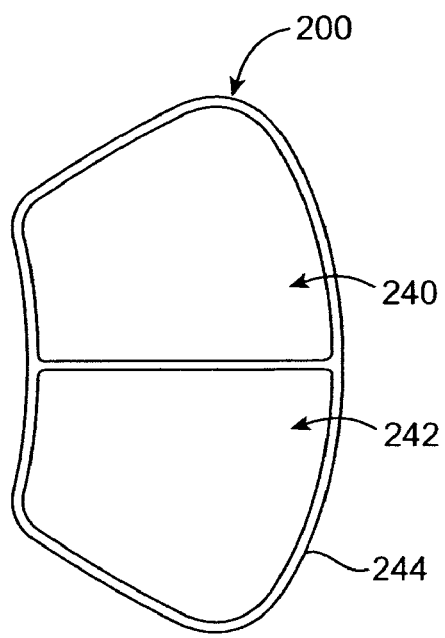
FIG. 14 illustrates a gastric balloon in accordance with the principles of the present invention including a pair of inflatable space-filling compartments contained by an external sheath.
Figure 15:
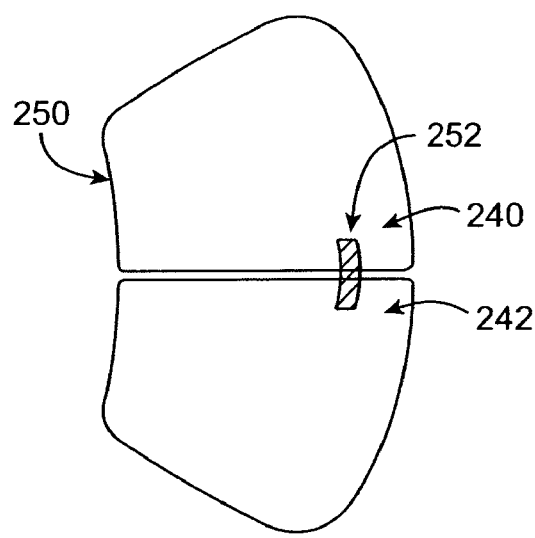
FIG. 15 illustrates a gastric balloon having two inflatable space-filling compartments joined together by a spine structure.

Referring now to FIGS. 14 and 15, the balloon 200 may comprise first and second internal inflatable compartments 240 and 242 having an external sheath or exoskeleton 244. The sheath 244 may be, for example, a non-distensible outer tubular structure having the desired crescent geometry, with the inflatable compartments 240 and 242 disposed therein. Alternatively, the exoskeleton could comprise a mesh, fabric, or other flexible containment member which holds the separate inflatable compartments 240 and 242 in place relative to each other. At least a portion of the exoskeleton 244 could be made to be non-collapsible in order to prevent accidental passage of the balloon through the pyloric valve in case of unintended deflation of both of the inflatable compartments 240 and 242.

The compartments 240 and 242 could also be held together by a spine element 250, as shown in FIG. 15. The balloons would be attached to the spine, optionally by heat sealing or adhesives, usually one or more fasteners 252, such as adhesive straps, are provided about the periphery of the inflatable compartments 240 and 242 to hold them together after deployment. The spine 250 can also optionally be used to receive and deploy inflation tubes, as described in more detail below.

Each of the balloons 200 described above will be provided with a valve mechanism or assembly to permit selective inflation with liquid fluids, gaseous fluids, or a combination thereof. If only a single inflatable compartment is utilized, the valving mechanism could be simply a one-way valve having a connector for releasably connecting to an inflation tube. For example, the inflation tube could be connected to the connector on the valve prior to introduction of the balloon in the patient's stomach. After introduction, the inflation medium could be introduced through the tube, and the tube detached and removed after inflation is complete. Optionally, the inflation tube could be introduced later for reinflation of the balloon if desired.

When two or more inflatable compartments, and optionally external bladders, are provided, the valve assemblies of the present invention will preferably provide for selectively delivering inflation medium to individual inflation ports on each of the inflatable compartments, external bladders, and optionally inflatable scaffolds. Inflation valves will usually comprise a one-way valve structure, such as a flap valve or a duckbill valve. The valves associated with each compartment will be arranged to permit manipulation of an associated inflation tube so that the valve is in line with an inflation port on the inflation tube to permit delivery of inflation medium.

In FIG. 16, for example, a first one-way valve 300 can be mounted on a wall of a first balloon compartment and a second one-way valve 302 can be mounted on the wall of a second balloon compartment. By then arranging the two valves in opposite directions along a common axis, an inflation tube 304 having a rotatable inflation port 306 can be disposed between the two valves. Then by turning the inflation tube, the first valve 300 or the second valve 302 may be selected to deliver inflation medium through the single inflation tube 304.

Alternatively, as shown in FIG. 17, a first inflation valve 310, a second inflation valve 312, and a third inflation valve 314, each of which is associated with a respective balloon compartment, may be axially arranged so that a single inflation tube 316 may be translated to successively access each of the one-way valves 310. In this way, each of the associated balloon compartments may be selectively inflated and reinflated by simply axially translating the inflation tube 316.

As a further alternative, as shown in FIG. 18, a single inflation tube 320 having multiple inflation ports 322, 324, and 326 may be disposed next to a linear array of balloon compartments and one-way inflation valves 330, 332, and 334. In this way, instead of axially translating the inflation tube 320, the valves can be selected by rotating the tube so that only a single inflation port is aligned with a single one-way valve at one time.

It will be appreciated that the above-described valve mechanisms and assemblies may be constructed in a wide variety of ways using a wide variety of one-way valve structures. For the purposes of the present invention, it is desirable only that the valve structures permit selective introduction of an inflation medium to individual balloon compartments using a single inflation tube. It will also be appreciated that more than one valve may be used in series (not shown) in place of a single valve to reduce further the potential for leakage of the filling media.

A first specific structure for implementing the inflation assembly of FIG. 16 is shown in FIG. 19. The inflation tube 304 having inflation port 306 is disposed between a wall 350 of a first balloon and a wall 352 of a second balloon. The first one-way valve 300 is positioned through the first wall 350, and the second one-way valve 302 is positioned through the second wall 352. Those valves are shown as duckbill valves. As shown in FIG. 19, the port 306 is aligned with the first one-way valve 300 so that introduction of a pressurized inflation medium through lumen 305 of the inflation tube 304 will open the duckbill valve and allow inflation medium to enter the first balloon. By then rotating the inflation tube 350 by 180° so that it is aligned with the second valve 302, inflation medium can be similarly delivered to the second balloon.

Figure 20:
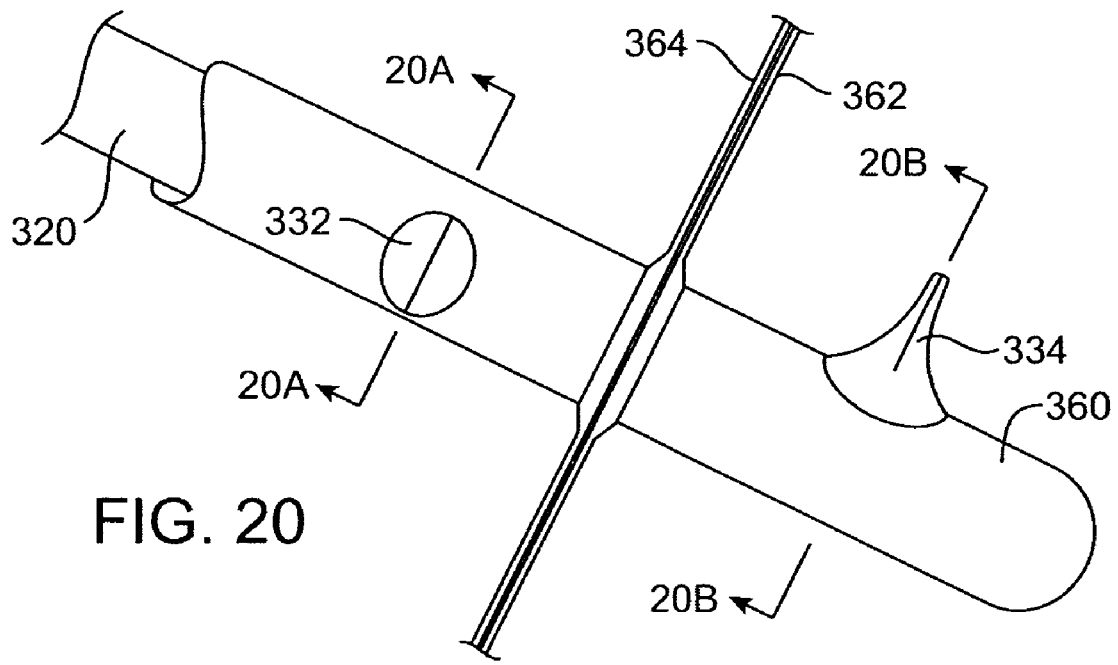
FIG. 20, 20A, and 20B illustrate an exemplary structure for valving according to FIG. 18.
Figure 20A:
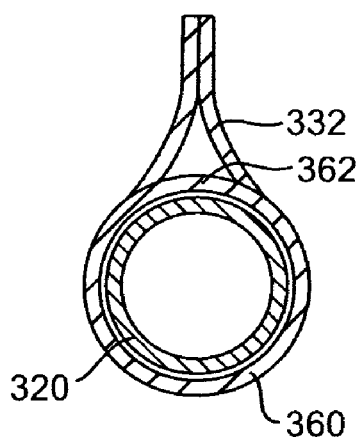
Figure 20B:
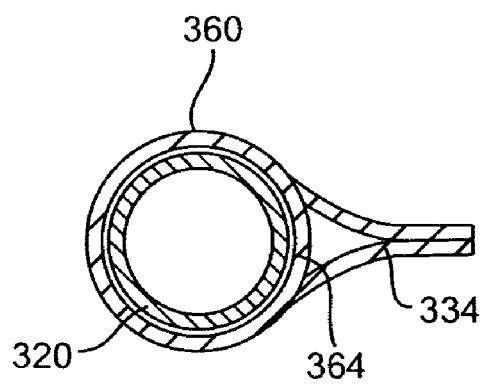

A specific valve system constructed generally as shown in FIG. 18 is shown in FIGS. 20, 20A and 20B. The inflation tube 320 is rotatably disposed within an outer tube 360 which passes between walls 362 and 364 of first and second inflatable compartments, respectively. The distal-most one-way valve 334 is disposed in a first radial direction on the outer tube 360, and the next inner one-way valve 332 is offset by 90°. The ports 362 and 364 on the inflation tube 320 (FIGS. 20A and 20B not illustrated) will be arranged so that in a first rotational position one port 362 is aligned with one-way valve 332 and in a second rotational position, a second port 364 is aligned with one-way valve 334. At no time, however, is more than one inflation port aligned with more than one one-way valve on the outer tube 360. Thus, by rotating inflation tube 320, individual inflatable compartments can be inflated.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for treating obesity in a patient, said method comprising:
   introducing a gastric balloon structure comprising a scaffold and at least two inflatable space-filling compartments to the inside of the patient's stomach;
   expanding the scaffold to provide a fixed support geometry within the stomach; and
   at least partly filling the at least two space-filling compartments of the balloon with a compressible and/or incompressible fluid such that the compartments are constrained by the scaffold after filling.

2. A method as in claim 1, further comprising determining the size of the stomach and selecting a gastric balloon of a proper size.

3. A method as in claim 2, wherein determining comprises visually examining the gastric cavity of the stomach through a gastroscope, externally scanning with X-rays, or externally scanning with ultrasound.

4. A method as in claim 2, wherein the size is determined while the stomach is filled with a biocompatible medium.

5. A method as in claim 4, wherein the balloon size is selected to leave an unobstructed stomach volume surrounding the sides of the device in the range from 10 cm3 to 100 cm3 after the balloon is inflated.

6. A method as in claim 4, wherein the space-filling compartments are filled with a mixture of compressible and incompressible fluid to control the buoyancy of the gastric balloon in the stomach.

7. A method as in claim 6, wherein the mixture of compressible and incompressible fluids is selected to provide a generally neutral buoyancy in the stomach.

8. A method as in claim 1, wherein introducing comprises passing the gastric balloon in a deflated configuration into the stomach through a gastroscope or using an orogastric or nasogastric tube.

9. A method as in claim 1, wherein the space-filling compartments and/or the scaffold is/are configured so that the gastric balloon structure will inflate with a curved geometry conforming to the curve of the gastric cavity.

10. A method as in claim 1, wherein the at least two space-filling compartments are inflated through an inflation tube removably attached to the balloon.

11. A method as in claim 10, further comprising selectively inflating each of the compartments by manipulating a valve structure which directs inflation fluid to a selected compartment.

12. A method as in claim 1, further comprising filling one or more external bladders attached to or over the outer surfaces of the space-filling compartments at least partially with a compressible and/or incompressible fluid.

13. A method as in claim 1, further comprising deflating all of the component structures and removing the deflated balloon from the stomach.

14. A method as in claim 13, wherein deflating comprises breaching one or more walls of each space-filling compartment.

15. A method as in claim 14, wherein breaching comprises severing a common wall portion between two or more space-filling compartments so that both deflate simultaneously.

16. A method as in claim 1, further comprising adjusting the fill volume of at least one space-filling compartment after filling has been completed.

17. A method as in claim 16, wherein fill volume adjusting comprises reattaching an inflation tube to one or more space-filling compartments, and filling or removing inflation fluid through the reattached inflation tube.

18. A method as in claim 1, wherein said scaffold structure has an interior and said space-filling compartments are constrained within the interior.

19. A method as in claim 1, wherein the gastric balloon structure floats free in the stomach after the scaffold is expanded and the space-filling compartments are filled.

20. A method for deploying a gastric balloon structure in a patient, said method comprising:
   introducing the balloon structure to the patient's stomach;
   filling a scaffold structure to provide a fixed support geometry; and
   separately filling a plurality of isolated chambers within the scaffold structure, wherein the chambers have individual volumes such that the collective volume of the chambers remaining inflated after the deflation of any single chamber is such that the balloon is prevented from passing through the pyloric valve.

21. A method as in claim 20, further comprising detecting a substance which is released into the stomach by a partially or fully ruptured balloon chamber and is excreted, secreted, exhaled, or regurgitated by the patient.

22. A method as in claim 21, wherein the substance is selected from the group consisting of dyes, scented materials, symptom-inducing agents, and detectable reactants.

23. A method as in claim 20, wherein at least some portions of the balloon are inflated in situ by inducing a gas-generating reaction within the balloon.

24. A method as in claim 20, wherein the scaffold structure has an interior and said isolated chambers are constrained within the interior after filling.

25. A method as in claim 20, wherein the gastric balloon structure floats free in the stomach after the scaffold is expanded and the space-filling compartments are filled.

* * * * *